US007660388B2

(12) United States Patent  
Gray

(10) Patent No.: US 7,660,388 B2
(45) Date of Patent: *Feb. 9, 2010

(54) INTEGRATED CARRY-ON BAGGAGE CART AND PASSENGER SCREENING STATION

(75) Inventor: Stephen J. Gray, Redondo Beach, CA (US)

(73) Assignee: Rapiscan Security Products, Inc., Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/171,343

(22) Filed: Jul. 11, 2008

(65) Prior Publication Data

US 2009/0041186 A1 Feb. 12, 2009

Related U.S. Application Data

(63) Continuation of application No. 11/364,926, filed on Mar. 1, 2006, now Pat. No. 7,418,077, which is a continuation-in-part of application No. 11/032,314, filed on Jan. 10, 2005.

(51) Int. Cl.
*G01N 23/04* (2006.01)
*G01T 1/00* (2006.01)

(52) U.S. Cl. ........................................ 378/57; 378/210

(58) Field of Classification Search .................. 378/57, 378/210

See application file for complete search history.

(56) References Cited

U.S. PATENT DOCUMENTS

| 4,711,994 | A | 12/1987 | Greenberg |
|---|---|---|---|
| 5,490,218 | A | 2/1996 | Krug et al. |
| 5,503,424 | A | 4/1996 | Agopian |
| 5,600,303 | A * | 2/1997 | Husseiny et al. ......... 340/568.1 |
| 5,838,758 | A | 11/1998 | Krug et al. |
| 6,094,472 | A | 7/2000 | Smith |
| 6,315,308 | B1 | 11/2001 | Konopka |
| 6,507,278 | B1 | 1/2003 | Brunetti et al. |
| 6,597,760 | B2 | 7/2003 | Beneke et al. |
| 6,665,373 | B1 | 12/2003 | Kotowski et al. |
| 7,092,485 | B2 | 8/2006 | Kravis |
| 7,110,925 | B2 | 9/2006 | Pendergraft et al. |
| 7,418,077 | B2 * | 8/2008 | Gray ........................... 378/57 |
| 2003/0025302 | A1 | 2/2003 | Urffer et al. |
| 2003/0171939 | A1 | 9/2003 | Yagesh et al. |
| 2003/0214407 | A1 | 11/2003 | Sweatte |
| 2003/0225612 | A1 | 12/2003 | DeSimone et al. |

(Continued)

OTHER PUBLICATIONS

International Search Report for PCT/US06/00623, Feb. 27, 2008, International Search Authority, pp. 12-13 of the report analyzes the materiality of certain references.

(Continued)

*Primary Examiner*—Edward J Glick
*Assistant Examiner*—Anastasia Midkiff
(74) *Attorney, Agent, or Firm*—PatentMetrix

(57) ABSTRACT

The present invention is directed towards apparatuses and methods for securing a location. Particularly, the present invention is directed towards methods, apparatuses, and integrated systems for the screening of individual passengers and their corresponding carry-on baggage carts with improved throughput, efficiency, and quality. In addition, the current invention is directed towards a carry-on baggage cart specifically designed for the disclosed integrated carry-on baggage cart and passenger screening system of the present invention.

17 Claims, 13 Drawing Sheets

U.S. PATENT DOCUMENTS

2003/0229506 A1    12/2003   Scott et al.
2004/0051265 A1*    3/2004   Nadeau .................... 280/47.35
2004/0120454 A1     6/2004   Ellenbogen et al.
2004/0252024 A1    12/2004   Huey et al.
2005/0024199 A1*    2/2005   Huey et al. ................ 340/521

OTHER PUBLICATIONS

Aviation Security Technologies and Procedures: Screening Passengers and Baggage, Oct. 26, 2001, Daniel Morgan: CRS Report for Congress.

* cited by examiner

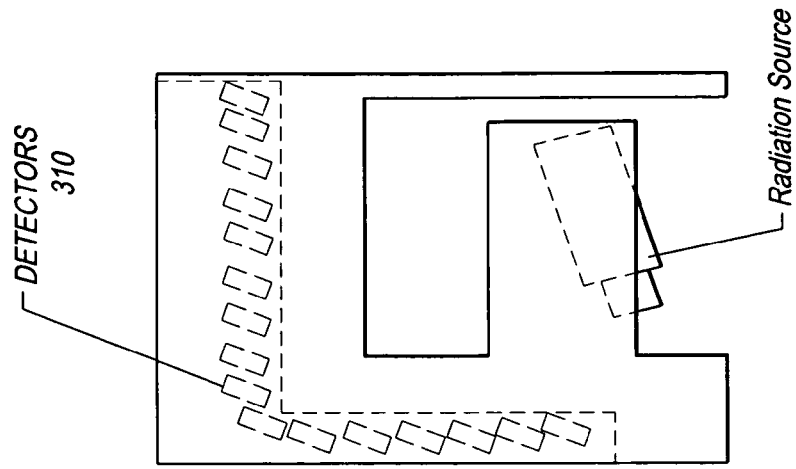
FIG. 3c
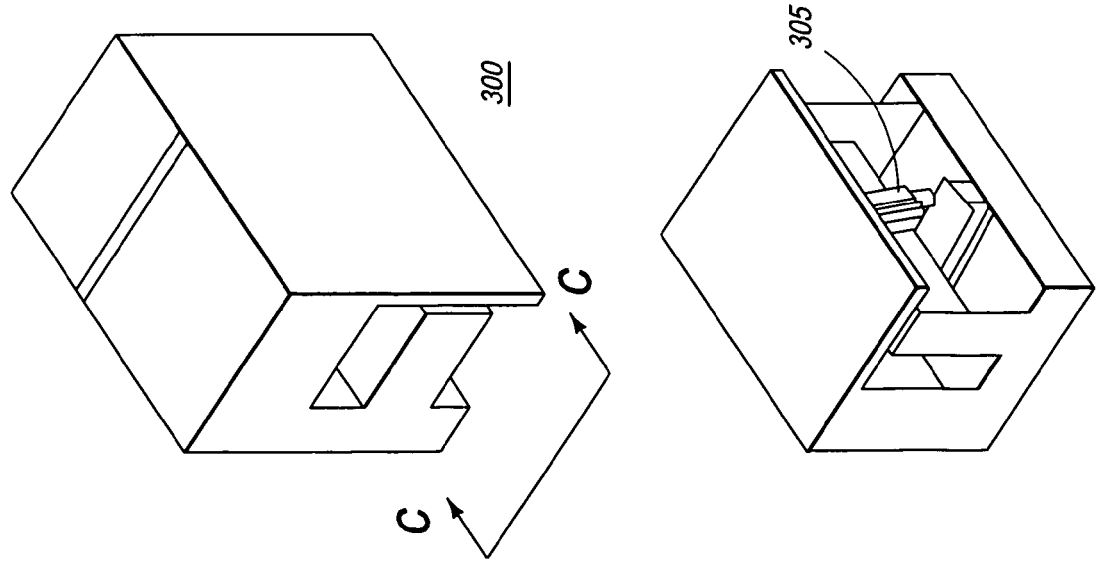
FIG. 3a
FIG. 3b

INTEGRATED CARRY-ON BAGGAGE CART AND PASSENGER SCREENING STATION

CROSS-REFERENCE TO RELATED APPLICATIONS

The present invention is a continuation of U.S. patent application Ser. No. 11/364,926, filed on Mar. 1, 2006, now U.S. Pat. No. 7,418,077 which is a continuation-in-part of U.S. patent application Ser. No. 11/032,314, filed on Jan. 10, 2005.

FIELD OF THE INVENTION

The present invention relates to an apparatus for, and a method of, securing a location. More specifically, the present invention is a method, apparatus, and integrated system for screening of individual passengers and their corresponding carry-on baggage carts with improved throughput, efficiency, and quality. The present invention also relates to a carry-on baggage cart specifically designed for the disclosed integrated carry-on baggage cart and passenger screening system.

BACKGROUND OF THE INVENTION

Locations must often be secured to ensure public safety and welfare. For example, places where there are large concentrations of people, such as airports or entertainment events, places that are of particular governmental importance, such as courthouses and government buildings, and other places where the threat of violence is high, such as prisons, require security measures to thwart dangerous or illegal activities. The primary security objective is to prevent the unauthorized entry of weapons, dangerous materials, illegal items, or other contraband into the location, thereby securing it. This is often achieved by requiring all people and items to enter into the location through defined checkpoints and, in those checkpoints, subjecting those people and items to thorough searches.

Currently, various devices are used to perform such searches. Regardless of the place of use, these detection systems are employed to detect the presence of contraband on the body or luggage of individuals entering the secure area. Contraband is not limited to weapons and arms, but rather it includes explosives (fireworks, ammunition, sparklers, matches, gunpowder, signal flares); weapons (guns, swords, pepper sprays, martial arts weapons, knives); pressurized containers (hair sprays, insect repellant, oxygen/propane tanks); poisons (insecticides, pesticides, arsenic, cyanide); household items (flammable liquids, solvents, bleach); and corrosives (acids, lye, mercury).

Such conventional security systems rely on data individually recorded by each security device to evaluate the performance of the specific device. For example, a metal detector with an embedded counter records and stores the number of people that passed through the metal detector in a given period of time. Similarly, a baggage screening X-ray machine records the number of bags passed through the system and the number of bags that possibly contained contraband.

In addition, screening checkpoints used in current security systems predominately operate using a single input and single output line approach. Each item must be thoroughly and individually scanned in the conventional systems. The complex security protocols being instituted require individuals to have each of their belongings, including laptops, shoes, coats, mobile phones, keys and other items, scanned by an X-ray scanner. It takes a considerable amount of time for individuals to divest themselves of their belongings and to remove laptops from their cases. This divestiture process tends to happen serially with individuals waiting in line until they have access to the machine. Contributing to the lag associated with the divestiture process, current systems employ a single conveyor belt, upon which each of the individual passenger items must be placed in order for the items to pass through the x-ray machine. Once the items are scanned, they accumulate on the opposite side of the scanning machine, thus creating "traffic" on the belt until retrieved by the passenger/owner. The belt must often be stopped by the operator to prevent the backlog of unclaimed baggage from reversing into the x-ray machine.

U.S. Pat. No. 6,472,984, assigned to Georal International Ltd., discloses a method of restricting access to an area comprising the steps consisting of: a) providing a chamber having one or more first doors and one or more second doors; b) opening said first doors to allow a person entry to the chamber from an infeed area; c) sensing for contraband as the person enters the chamber; d) if no contraband was sensed during entry to the chamber, closing the first door and opening said second door to allow the person access to the protected area, but if contraband was sensed maintaining said second door closed and allowing the first doors to open to provide access from the chamber to the infeed area; and e) detecting the presence of objects remaining in said chamber after the person has vacated the chamber, and inhibiting opening of at least one of said doors if an object is detected in said chamber.

U.S. Pat. No. 6,484,650, assigned to Gerald Stomski, describes a security system for monitoring and protecting personnel in an area including at least one queue of successively arriving individuals, comprising: a plurality of at least three contiguous chambers, including an entry chamber, an exit chamber and at least one intermediate chamber, wherein said chambers are arranged in a matrix of at least two parallel lines of chambers so as to receive at least two parallel queues of successively arriving individuals, said chambers each having bullet-proof transparent walls and bullet-proof doors, said doors including: an entry door to the entry chamber, an exit door from the exit chamber, a common door between each intermediate chamber and a said contiguous chamber, said doors having remotely controlled locks, means for monitoring a selected individual in a selected chamber, and an automated door interlock system arranged and adapted to remotely unlock selected locks to pass individuals successively through said chambers, and to lock selected locks to detain selected individuals during monitoring.

U.S. Pat. No. 6,308,644, assigned to William Diaz, discloses an access control vestibule, comprising; a vestibule frame configured to form said access control vestibule mounted in said vestibule frame; an entrance door and an exit door; an entrance door frame and an exit door frame; a panel mounted in said vestibule frame and forming a side wall section of said vestibule; said entrance door and said exit door being formed by a panel mounted in each of said door frames; locks associated with said entrance door and said exit door; a metal detector located to detect a metal object being disposed between said entrance and exit doors; control means to prevent both doors from being unlocked at the same time, and to prevent said exit door from being unlocked when said metal detector detects a metal object; said entrance door and said exit door both being manually operated; and said entrance door and said exit door each being formed by a single swinging door, and swingable towards the outside of said vestibule.

U.S. Pat. No. 4,357,535, assigned to Scan-Tech Security, L.P., discloses an "apparatus for inspecting an article comprising a longitudinally extending cabinet having top and bottom walls, oppositely disposed side walls, and oppositely disposed end walls; a longitudinally extending slot-like opening in said cabinet adjacent a corresponding edge of said top wall and a side wall; an entrance opening at one portion of said cabinet and an exit opening at another portion of said cabinet, said entrance opening and said exit opening connecting with said longitudinal opening so that a hand-held suspended article can be passed in said cabinet by a person holding said article outside said cabinet; means arranged within said cabinet for generating sensing radiation in a direction transversely to movement of said hand-held article; and means for detecting said radiation after passage through said article and for recording resulting information." More specifically, the '535 patent describes an inspection system for simultaneously inspecting hand carried articles and providing metal detection of the person carrying said articles. Metal detection of the person is accomplished independently by walking through a metal detector arch.

The conventional prior art security baggage and passenger screening systems described above are inefficient in the manner in which they are set up to receive and distribute both passengers and their carry-on baggage. As mentioned above, the security protocols of conventional prior art screening systems require individuals to have each of their belongings, including laptops, shoes, coats, mobile phones, keys and other items, scanned by an X-ray scanner. It takes a considerable amount of time for individuals to divest themselves of these belongings. This divestiture process tends to happen serially with individuals waiting in line until they have access to the machine. Thus, X-ray machine operators spend more time waiting for passengers to divest themselves of their belongings and load them onto the conveyor than scanning bags.

In addition to the lag associated with the divestiture process, current systems employ a single conveyor belt, upon which each of the individual passenger items must be placed in order for the items to pass through the x-ray machine. Once the items are scanned, they accumulate on the opposite side of the scanning machine, thus creating "traffic" on the belt until retrieved by the owner. The resultant scanned baggage belonging to passengers that have been selected for additional hand searching wait at the X-ray system's exit conveyor until those passengers are thoroughly searched. Thus, the bags are left on the conveyor for approximately at least 1.5-2.0 minutes, thereby causing a back-up that forces the X-ray machine operator to have to wait until such back-up is cleared. The belt must often be stopped by the operator to prevent the backlog of unclaimed baggage from reversing into the x-ray machine.

Thus, even when individual passengers have access to the machine, the process is still time-consuming as each individual item to be scanned must be placed on the single conveyor belt and then collected by the owner. This is especially true for Computerized Tomography (CT) scanning systems, which are much slower in operation compared with conventional X-ray scanning systems. CT scanning systems are being used more frequently in airport baggage scanning scenarios. In addition to the time it takes for the machine to operate, it may take some time for a passenger to reclaim and collect his baggage and other personal belongings, further creating a backlog in the scanning system. In addition, such existing systems tend to have many other problems, including for example, several security personnel having excessive downtime and a necessity for a dedicated operator for each detector to direct traffic.

Additionally, passengers lack sufficient information regarding how to most efficiently pass through a baggage checkpoint or screening station. For example, passengers may wait in a screening station or checkpoint lane full of passengers while a second lane remains completely empty, thereby causing unnecessary delay. Thus, the much desired streamlined and efficient function of the scanning operation is hampered. Current systems lack appropriate means for indicating whether lanes, among a plurality of check station lanes, are operational or closed.

Furthermore, passengers lack information regarding what items should be subjected to CT scanning, x-ray scanning, metal detection, or hand searching, such as large buckle belts or shoes. The presence of portable computing devices, such as laptops, further causes more delay. It takes a considerable amount of time for individuals to remove laptops from their cases. Generally, as described above, portable computing devices must be removed from their carrying case and placed into bins or drawers so that they can be scanned singularly. Passengers often fail to efficiently remove such items from their carrying cases and, consequently, do not proceed through the scanning checkpoint efficiently. Individual passengers thus wait in line until they have access to the machine.

Additionally, those areas contained within the scanning checkpoint or check station areas specifically allocated for passengers to divest themselves of their belongings are not set up to facilitate rapid and efficient divestiture of passenger belongings. In conventional systems, such areas consist of tables located in front of or around the conveyor belt scanner, thus causing those slower passengers to block the line from moving at a reasonable and efficient pace. Along the same lines, the problem also presents itself when passengers collect their belongings and reload their items and replace portable computing devices in their cases. Individual passengers also lack proper instruction on where to stand so as not to obstruct the natural flow of the X-ray scanning system line.

Conventional security screening systems lack appropriate means for handling carry-on baggage in its entirety prior to and/or during scanning. Traditional carry-on baggage carts are cumbersome and bulky in dimension, including towable, portable, or mobile carts. These carry-on baggage carts present problems when scanned in conventional scanning systems. For example, the design of the carts does not allow for conventional scanning systems to sufficiently scan due to the inadequate positioning of the carry-on baggage. This, in turn, leads to the capturing, storing, processing and development of incomplete and imprecise X-ray images. In addition, the carry-on luggage carts require a larger X-ray apparatus to be scanned completely. Metal bars of existing cart designs may also hinder the path of the X-ray, thus obscuring some of the items placed on the cart from scanning. This also leads to imprecise capturing, storing, processing and development of x-ray images. In addition, in scanning conventionally designed carry-on baggage carts, it is difficult to contain the x-ray radiation; to scan an existing, conventional carry-on baggage cart, the x-ray machine would need a large opening. Thus, in such systems, costly safeguards would need to be implemented to protect the general public and x-ray operators.

Despite these prior art efforts to improve methods, apparatuses, and systems for scanning carry-on baggage, the abovementioned problems have not been solved. The prior art methods fail to disclose methods and systems that alleviate delay during the divestiture process. In addition, the prior art does not improve the overall efficiency and throughput of the system.

Thus, there is a need for an improved security check station that reduces the waiting time for individuals and has improved throughput and efficiency. Such a system would reduce over-staffing of security personnel, facilitate automation of the metal detector, curtail idle time of machine operators, and significantly increase throughput of the machines due to decreased back-up of the conveyor system. In a scanning system with improved throughput and efficiency, it is possible to reduce the total number of scanning stations required at any one location. In addition, with shorter lines of people waiting for baggage and body scans, less floor space is required.

Additionally, there is a need for methods or systems of integrating data from multiple security devices dynamically and communicating such data to a plurality of users, in order to enable effective security. In particular, there is a need for integrating scan data from individual passenger scans with carry-on cart baggage data from such a screening system to correlate the data.

There is also a need for an intelligently managed security system, where the plurality of information is centrally processed for yielding specific outputs to different users. Also, there is a need to correlate the scanning data of different entities to improve the security level.

In addition, there is a need for methods and systems which employ a Computed Tomography (CT) scanner in an integrated carry-on baggage cart and passenger screening station.

There is also a need for a carry-on baggage cart that is capable of being collapsed, thus allowing the cart and its contents to pass through the CT scanner.

There is also a need for a carry-on luggage cart that is X-ray transmissive to allow for the CT scanner to rotate and scan completely around the cart.

There is also a need for a method and system for increasing the security associated with an integrated carry-on baggage cart and passenger screening station, in which passengers are associated with their corresponding carry-on baggage cart.

SUMMARY OF THE INVENTION

The present invention is directed toward an integrated security checkpoint that can screen both individual passengers and carry-on carts containing their baggage. The methods, apparatuses, and systems of the present invention enable the efficient scanning of both individual passengers and their respective carry-on carts in the same secure area by providing individual passengers with a screening cart, permitting passengers to send the screening cart through an X-ray imaging machine, and permitting passengers to walk through an adjacent metal detector where, once cleared, the individual passenger can retrieve his or her screening cart.

In one embodiment, the present invention is directed towards a method for conducting security comprising the steps of providing a person to be screened with a screening cart wherein the screening cart is a frame assembly designed to physically complement an X-ray scanning system; providing a conveyer mechanism that directs the screening cart through an X-ray scanning system; inspecting the contents of the screening cart and delivering the screening cart to the passenger. The method further includes directing a passenger to walk through a passenger screening device. In one embodiment, the passenger screening device is a metal detector. In another embodiment, the passenger indicates that the passenger is ready to be screened.

In another embodiment of the method for conducting security, the screening cart is a frame assembly designed with collapsible legs. The screening cart is also designed to stack into other screening carts for storage.

Preferably, the cart is comprised of an X-ray transmissive material, such as carbon fiber or transparent synthetic resin.

In one embodiment of the method for conducting security, the X-ray scanning system comprises a radiation source and a detector array. The radiation source is a dual energy source. In one embodiment, the X-ray scanning system comprises any one or a combination of Computerized Tomography (CT) scanning systems, quadrupole resonance systems, X-ray diffraction systems and X-ray backscatter systems.

In another embodiment, the present invention is directed towards a system for conducting security, comprising an X-ray scanning system which further comprises an entrance designed to physically complement a screening cart frame assembly; a guide mechanism to direct a screening cart passing through the X-ray scanning system; and a mechanism for delivering the screening cart to the passenger after both passenger and cart have been screened. Preferably, the X-ray scanning system comprises a radiation source and a detector array. The radiation source is preferably a dual energy source. In one embodiment, the X-ray scanning system comprises a radiation source and a detector array. The radiation source is a dual energy source. In one embodiment, the X-ray scanning system comprises any one or a combination of Computerized Tomography (CT) scanning systems, quadrupole resonance systems, X-ray diffraction systems and X-ray backscatter systems.

In one embodiment, a passenger screening device, such as but not limited to a metal detector, is provided.

In one embodiment, the screening cart comprises a frame assembly designed with collapsible legs. The screening cart is also designed to stack into other screening carts for storage. Preferably, the cart is comprised of an X-ray transmissive material.

In another embodiment the present invention is directed towards a method for conducting security comprising the steps of providing a person to be screened with a screening cart wherein the screening cart is a frame assembly designed to physically complement the entry gate and internal configuration of an X-ray system; providing a conveyor mechanism that directs the screening cart through an X-ray scanning system; delivering the screening cart to the passenger; inspecting the contents of the screening cart; indicating to a passenger to walk through a passenger screening device; delivering the screening cart to the passenger, after both passenger and cart have been screened; and integrating data collected from both X-ray scanning system and passenger screening device to generate overall threat assessment.

Preferably, the X-ray scanning system comprises a radiation source and a detector array. The radiation source is preferably a dual energy source. In one embodiment, the X-ray scanning system comprises any one or a combination of Computerized Tomography (CT) scanning systems, quadrupole resonance systems, X-ray diffraction systems and X-ray backscatter systems.

In one embodiment, a passenger screening device, such as but not limited to a metal detector, is provided.

In one embodiment, the screening cart comprises a frame assembly designed with collapsible legs. The screening cart is also designed to stack into other screening carts for storage. Preferably, the cart is comprised of an X-ray transmissive material.

In another embodiment, the present invention is directed towards a system for conducting security, comprising an X-ray scanning system further comprising an entrance designed to physically complement a screening cart frame assembly; a guide mechanism to direct a screening cart passing through the X-ray scanning system; a passenger screening device; a mechanism for delivering the screening cart to the passenger after both passenger and cart have been screened;

and an integrated screening station for integrating data collected from both X-ray scanning system and passenger screening device to generate overall threat assessment.

Preferably, the integrated screening station comprises a central server, further comprising a processor and a memory in data communication with the X-ray scanning system and the passenger screening device.

In an exemplary embodiment, the X-ray scanning system comprises a radiation source and a detector array. The radiation source is preferably a dual energy source. In one embodiment, the X-ray scanning system comprises any one or a combination of Computerized Tomography (CT) scanning systems, quadrupole resonance systems, X-ray diffraction systems and X-ray backscatter systems.

In one embodiment, a passenger screening device such as, but not limited to, a metal detector is provided.

In one embodiment, the screening cart comprises a frame assembly designed with collapsible legs. The screening cart is also designed to stack into other screening carts for storage. Preferably, the cart is comprised of an X-ray transmissive material.

In one embodiment, the integrated carry-on cart and passenger screening station of the present invention further comprises enhanced security. In one embodiment, the security enhancement comprises a bar code reader.

In one embodiment, the bar code reader is located at a cart access station, where the passenger retrieves an empty cart. In one embodiment, the bar code reader is used to register passenger information into a database to associate a cart with a passenger. In one embodiment, the passenger information is associated with a cart by scanning the passenger's boarding pass underneath the bar code reader.

In one embodiment, the carry-on cart, in any configuration, may optionally include a small computer with a display for displaying the information scanned from the passenger, such as, but not limited to, passenger name, flight information, and the like.

In one embodiment, the carry-on cart employed in the present invention may further comprise a cover. In one embodiment, the cover further comprises a roll-top or netting. In one embodiment, the cover automatically locks when the passenger closes it after he finishes the divestiture process. In one embodiment, after the scanning process is complete, the passenger can "unlock" the cart cover by simply waving the bar code on his boarding pass underneath the bar code reader that is fixedly attached to the small computer on the cart.

BRIEF DESCRIPTION OF THE DRAWINGS

These and other features and advantages of the present invention will be appreciated, as they become better understood by reference to the following Detailed Description when considered in connection with the accompanying drawings, wherein:

FIGS. 3a, 3b, and 3c illustrate various perspective views of an X-ray imaging system as used in the carry-on baggage cart screening portion of the integrated screening system of the present invention;

DETAILED DESCRIPTION OF THE INVENTION

Figure 1:
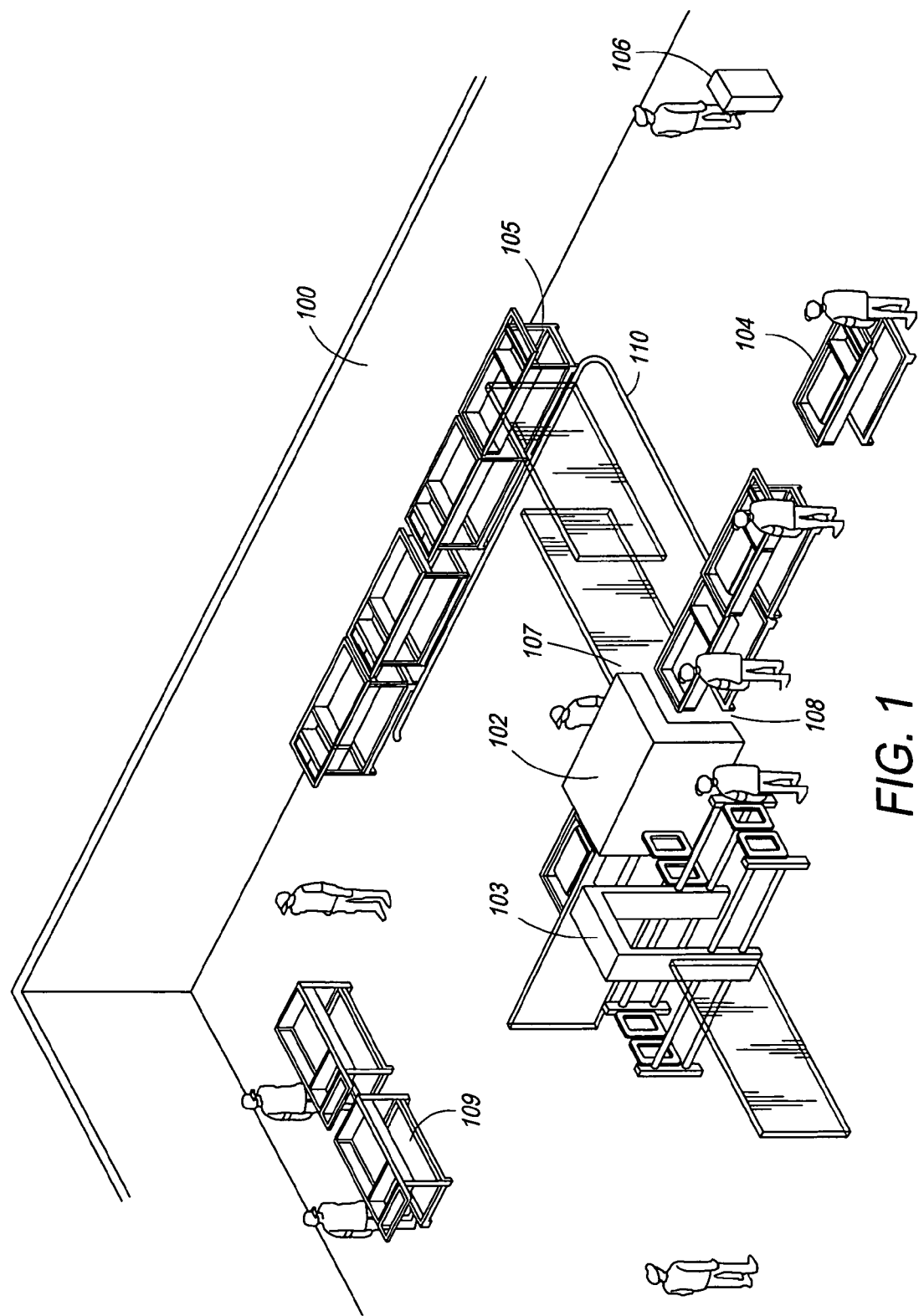
FIG. 1 is a top perspective view of one embodiment and functional layout of an integrated carry-on baggage cart and passenger screening station, facilitating screening of both carry-on luggage placed on the screening cart and individual passengers.

The present invention is directed towards a high throughput screening system that improves the efficiency, technique, and quality of passenger and carry-on baggage scanning at secure locations. Although the system of the present invention has many applications, an exemplary embodiment will be described with particular reference to its application to an airport security system. One of ordinary skill in the art would appreciate the present invention may be applied to a plurality of other security environments, including prisons, government buildings, other buildings requiring secured access, and entertainment venues.

As used here, the term "baggage" refers to any type of carry-on item as is conventionally allowed in various locations, including, but not limited to smaller sized luggage, laptop cases, purses, briefcases, umbrellas, handbags, large coats, and in some cases, shoes. Generally, these items are required to be removed from the individual prior to entrance into the metal detector area. In addition, while the terms "individual" and "passenger" are used interchangeably, it is to be understood by those of ordinary skill in the art that any living entity may be screened for any reason in the metal detector portion of the system of the present invention and constitutes an individual or passenger.

The screening system of the present invention comprises a plurality of screening devices, including, but not limited to, metal detectors, X-ray imaging systems, baggage trace detectors, trace portals, personnel scanners, X-ray diffraction systems, CT systems, and personnel identification systems. In one embodiment, the screening system of the present invention employs both a passenger metal detector system and a carry-on cart baggage scanning system. Thus, both the passenger and their baggage may be screened efficiently. In addition, the present invention optionally employs a method for integrating the information from the two detection sources, thus enabling a more accurate threat level determination.

More specifically, the present invention discloses novel methods, apparatuses, and systems facilitating screening of both individual passengers and their carry-on luggage carts thus improving the efficiency and throughput of the screening system. Preferably, the scan data from the carry-on baggage cart screening system and the individual passenger screening system are transmitted to a central server by any method known to one of ordinary skill in the art.

Optionally, the present invention may associate assessment data of two or more entities to evaluate the overall threat level of a plurality of entities, wherein the entity can be an individual or a bag. Simply evaluating the threat level associated with each individual based upon the metal content possessed by that individual may not be sufficient.

In current security systems, the X-ray screening system can be a bottleneck relative to the entire screening system. It takes a considerable amount of time for individuals to divest themselves of their personal belongings including shoes, coats, keys, and phones and to remove laptops from their cases for X-ray screening of these items. This series of operations tends to happen serially with everyone waiting in line until they have access to the machine and it is their turn to divest. This is followed by the need to reconcile the passenger items after screening that, again, creates delays in the check station flow.

Operationally, it is preferred that passengers are positively linked to their belongings, including luggage, bags, and other personal items. Personal belongings not subject to a baggage claim check or other tag may be linked to specific passengers by tagging each personal belonging at the security checkpoint or check station. It is preferred, however, to associate passengers with their belongings using a form of physical association. In one embodiment, a passenger divests themselves of personal belongings by placing all appropriate items into the first stage screening device, such as on the carry-on baggage cart, or screening cart, capable of passing through the X-ray screening machine via a floor conveying mechanism with guide rails. While the first stage screening device is conducting a scan on the passenger's carry-on baggage, that particular passenger is preferably directed to walk through the metal detector via a gate mechanism, which is further described in detail below. Succeeding passengers are prevented from taking any action by a gate or light. After the first individual and their belongings successfully pass through the first stage screening process and, accordingly, a second gate, light, or area, a subsequent individual is allowed to enter the first stage screening process.

Reference will now be made in detail to specific embodiments of the invention. While the invention will be described in conjunction with specific embodiments, it is not intended to limit the invention to one embodiment.

FIG. 1 illustrates a top perspective view of one embodiment and functional layout of an integrated carry-on baggage cart and individual passenger screening station 100, facilitating thorough screening of both carry-on baggage placed on the cart and passengers. Integrated screening station 100 comprises a central server 101 (not shown), which has a processor 101a (not shown) and a memory 101b (not shown) in data communication with at least two screening devices. In one embodiment, the two screening devices comprise an X-ray imaging system 102, such as a C-frame X-ray imaging system, and passenger screening metal detector 103. X-ray baggage screening system 102 is designed to accept carry-on baggage carts, as will be described in further detail below. One of ordinary skill in the art can appreciate that a plurality of screening devices may be incorporated in the system without departing from the spirit and scope of the invention.

Processor 101a can execute a plurality of different calculations, processes, and/or algorithms to evaluate the assessment data received from the plurality of devices. In one embodiment, the assessment data is evaluated according to a fuzzy logic algorithm based upon rules established governing the meaning of individual features. Alternately, a neural network may be employed to evaluate the data. Alternatively, the data may be evaluated by an automated classification system.

The abovementioned approaches of threat evaluation improve the level of security because data from multiple screening devices can be integrated to determine if a threat level exists. In particular, the integration of data from multiple screening devices aids in efficiently handling circumstances whereby an individual is cleared by each screening device independently but, in combination, represents a sufficient threat requiring subsequent analysis.

Passengers, once having entered integrated screening station 100, perform a few mandatory tasks, in part or wholly manual, including, but not limited to, pulling carry-on cart or screening cart 104, (described in greater detail with respect to FIG. 2) from empty carry-on cart area 105 and subsequently loading carry-on cart 104 with personal belongings in loading area 106 for entrance into inspection area 107. Carry-on cart or screening cart 104 is screened through inspection area 107 via C-frame X-ray imaging system 102, described in greater detail below with respect to FIG. 3. Individual passengers are directed to walk through metal detector 103, which is also described in greater detail below with respect to FIG. 5.

Each screening device has an associated memory and processing power that is used to evaluate the threat level associated with an entity, being scanned or detected, and to determine the value of assessment data to be transferred preferably to central server and/or other devices. Thus, central server 101 optionally aggregates data received from the plurality of screening devices 102 and 103, and uses a set of pre-defined processes to determine the overall threat level associated with the scanned entity. Once determined, an alarm, status signal, or other threat indicator information is communicated to an indicator system (not shown). One of ordinary skill in the art would appreciate that central server 101 could optionally be physically combined with one of the screening devices and need not be independent or separate from any or all of the devices.

Assessment data is received by the central server 101 from the employed screening devices, via a transceiver, into memory 101b. Preferably, each device, including X-ray imaging system 102, metal detector 103, and optional devices, such as but not limited to, a trace detector, are capable of transmitting data in a real-time manner to the central server 101 and/or every other device present in the system. Memory 101b is in data communication with a processor 101a capable of executing code to determine a total threat level based upon the individual device assessment data received. The memory 101b and processor 101a may be incorporated into one of the screening devices or be embodied in central server 101 that is in data communication with the plurality of screening devices.

Carry-on baggage cart 104 is designed to pass through the suitably designed C-frame X-ray imaging system 102 via a conveyance mechanism 108, such as, but not limited to a guide rail mechanism. If no item of threat or concern is detected in any of the screening devices, the carry-on baggage cart and/or passenger are cleared. Upon detection of an item of threat or concern, the entire carry-on baggage cart and/or passenger is tagged as suspect and taken to a designated search area, whereby the individual or carry-on baggage are subjected to further manual search. Subsequently, passengers off-load carts 104 in a designated area 109, away from the screening area, thereby preventing congestion. Eventually, carts are put back into use via the cart mover portion 110 of the conveyance mechanism.

In an exemplary embodiment the carry-on baggage cart or screening cart is of a three-dimensional (3-D) configuration allowing it to fit and thus pass through the preferably custom-designed entry gate of the C-framed X-ray imaging system implemented in accordance with the present invention and as described in further detail with respect to FIG. 3. Preferably, the screening cart is substantially a frame assembly and designed to physically complement the entry gate and internal configuration of the X-ray system. In one embodiment, the carry-on baggage cart comprises a novel "C"-configuration and fits into a "C"-configured entry gate of the X-ray imaging system thereby traversing the inspection area of the X-ray imaging system. A "C" configuration of the carry-on baggage cart also keeps the members or bars comprising the frame assembly of the cart away from the X-ray path, thus facilitating appropriate positioning of the carry-on items that are placed upon it. This, in turn, assists in accurate scanning of the contents of the carry-on baggage cart via X-ray, thus leading to the capturing, storing, processing and development of complete X-ray images.

Figure 2:
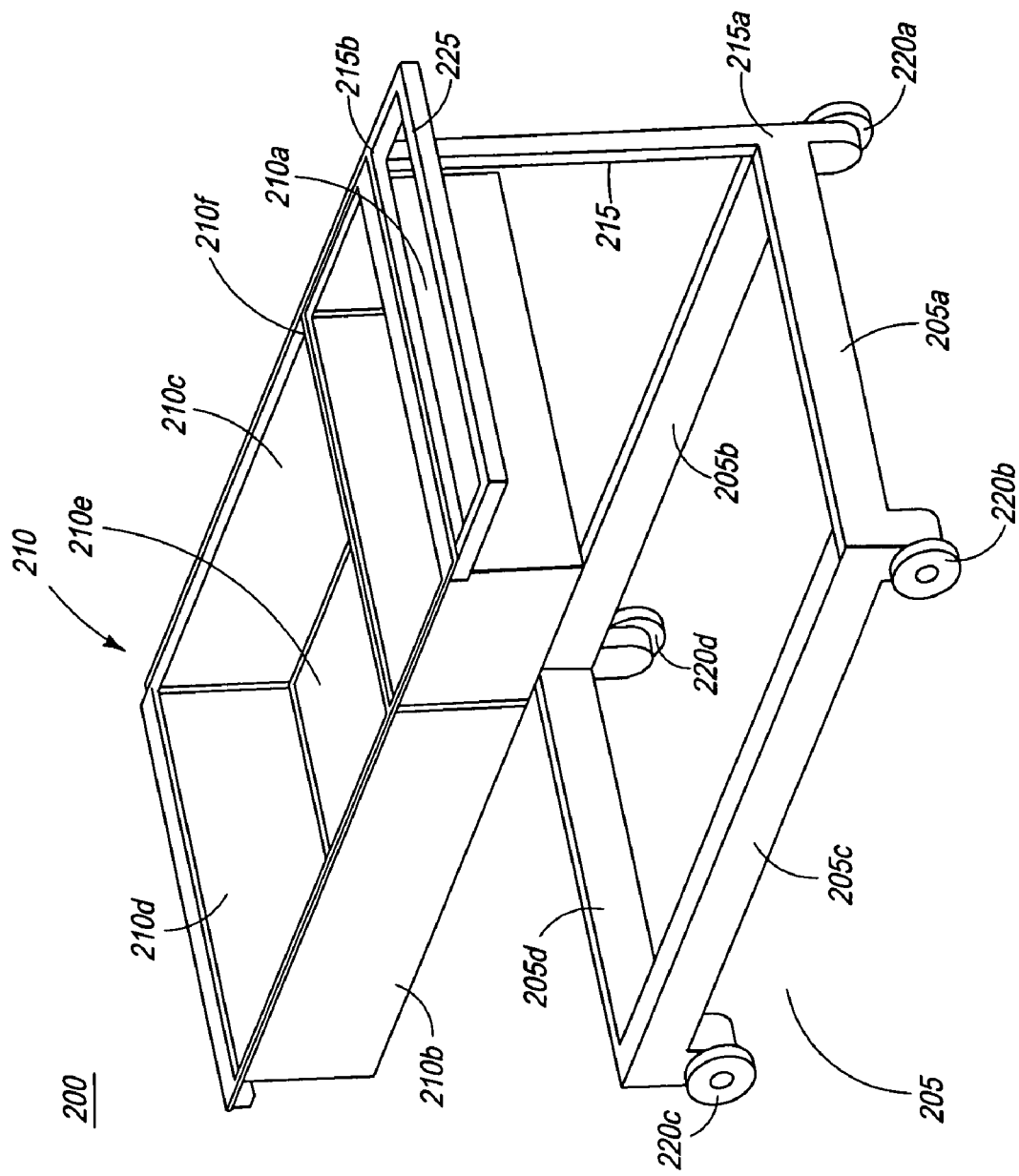
FIG. 2 is a perspective view of a carry-on baggage cart or screening cart configuration as used in the present invention.

Referring now to FIG. 2, a perspective view of an exemplary carry-on baggage cart as used in the present invention is depicted. Carry-on baggage cart 200 comprises a substantially connected frame assembly with substantially rectangular base 205 and substantially rectangular drawer (or bin or tray) 210, integrally connected by connecting vertical arm 215, thus forming a "C"-shape frame assembly. Preferably carry-on baggage cart 200 is of the following material and constructional specifications: rigid and lightweight metallic material such as, but not limited to, stainless steel or aluminum. A person of ordinary skill would appreciate that the materials used for the cart are not limited to the abovementioned metallic materials and can be easily adjusted to suit varied operational requirements and specifications.

Although cart 200 is preferably constructed in the form of a three-dimensional "C"-shape, a variety of other design approaches may be adopted for the construction of the carry-on baggage cart and its corresponding X-ray screening system and are readily apparent to persons of ordinary skill in the art.

In one embodiment, carry-on baggage cart 200 comprises a three-dimensional "C"-shaped frame assembly. Carry-on baggage cart 200 comprises base 205 and drawer 210 integrally connected by vertical connecting arm 215. Cart base 205 preferably comprises wheels 220*a*, 220*b*, 220*c*, and 220*d*. While it is preferred that carry-on baggage cart 200 is propelled via wheels, one of ordinary skill in the art would understand that any other conveyance mechanism may be employed in the present invention. Cart base 205 further comprises four side bars or members 205*a*, 205*b*, 205*c*, and 205*d* which are laterally connected to one another. Side members 205*a*, 205*b*, 205*c*, and 205*d* may optionally be connected to a floor base 205*e* (not shown). Side members 205*a* and 205*d* are preferably parallel to each other. Side members 205*b* and 205*c* are preferably parallel to each other. Side member 205*a* is preferably perpendicular to side members 205*b* and 205*c*. Side member 205*d* is also preferably perpendicular to side members 205*b* and 205*c*, thus forming a rectangular base.

The bottom end 215*a* of integrally connecting vertical arm 215 is connected to proximal side member 205*a* of cart base 205, just above wheel 220*a*. The top portion 215*b* of connecting vertical arm 215 is fixably connected to drawer 210, at its proximal end 210*a*. Drawer 210 has four side walls 210*a*, 210*b*, 210*c*, and 210*d* which are fixably and adjacently connected to one another. In addition, four side walls 210*a*, 210*b*, 210*c*, and 210*d* are integrally connected to drawer base 210*e*. Drawer 210 may further be compartmentalized by an additional retaining wall, such as 210*f*. Drawer 210 or parts thereof may optionally be removable for ease of loading and unloading carry-on items. In addition, drawer 210 may optionally comprise a lockable cover (not shown) for additional security of personal items. Drawer 210 is preferably rectangular in form, such as with cart base 205, wherein side walls 210*a* and 210*d* may be shorter in length than walls 210*b* and 210*c*, although a variety of shapes may be readily apparent to those of ordinary skill in the art.

FIGS. 3*a*, 3*b*, and 3*c* illustrate various perspective views of the C-frame X-ray imaging system as used in the carry-on baggage screening portion of the integrated screening system of the present invention. As described with respect to FIGS. 3*a* and 3*b*, X-ray imaging system 300 comprises a radiation source 305 and an X-ray detector array 310. Preferably, the X-ray imaging system 300 employed is of a backscatter detection type. Depending on the design of the corresponding cart, radiation source 305 can be located either above or below the drawer of the carry-on cart shown in FIG. 2. The array of detectors is preferably above or below the cart, also depending upon the placement of the radiation source 305.

In one embodiment, radiation source 305 is an X-ray generator. The source of radiation includes radio-isotopic source, an X-ray tube or any other source known in the art capable of producing beam flux and energy sufficiently high to direct a beam to traverse the space through the carry-on baggage cart and the contents of the cart to detectors at the other side. The choice of source type and its intensity and energy depends upon the sensitivity of the detectors, the radiographic density of the cargo in the space between the source and detectors, radiation safety considerations, and operational requirements, such as the inspection speed. One of ordinary skill in the art would appreciate how to select a radiation source type, depending upon his or her inspection requirements.

In an optional embodiment, the radiation source may be a dual energy radiation source which employs respectively different radiation energies or two detector systems, having varying sensitivities to differing radiation energies. By comparing at least two congruent radiation images that were obtained with respectively different radiation energies, it is possible to discriminate articles having low and high ordering number. Organic materials, such as drugs and explosives, can thus be better distinguished from other materials, for example metals (weapons).

While not shown in FIGS. 3*a*, 3*b*, and 3*c*, X-ray imaging system 300 also comprises a floor conveyance mechanism, further comprising guide rails for accepting the wheel mechanism of the carry-on baggage cart, both of which are described in further detail below.

As shown in FIG. 3*c*, the X-ray imaging system 300 comprises detector array 310. FIG. 3*c* is a two-dimensional side perspective view of the X-ray imaging machine shown in FIG. 3*a*. Preferably, detector array 310 is an "L"-shaped array, as shown. Detectors 310 may be formed by a stack of crystals that generate analog signals when X-rays impinge upon them, with the signal strength proportional to the amount of beam attenuation in the object under inspection. In one embodiment, the X-ray beam detector arrangement consists of a linear array of solid-state detectors of the crystal-diode type. A typical arrangement uses cadmium tungstate scintillating crystals to absorb the X-rays transmitted through the OUI and to convert the absorbed X-rays into photons of visible light. Crystals such as bismuth germinate, sodium iodide, or other suitable crystals may be alternatively used as known to a person of ordinary skill in the art. The crystals can be directly coupled to a suitable detector, such as a photodiode or photo-multiplier. The detector photodiodes could be linearly arranged, which through unity-gain devices, provide advantages over photo-multipliers in terms of operating range, linearity and detector-to-detector matching. In another embodiment, an area detector is used as an alternative to linear array detectors. Such an area detector could be a scintillating strip, such as cesium iodide or other materials known in the art, viewed by a suitable camera or optically coupled to a charge-coupled device (CCD).

Figure 4:
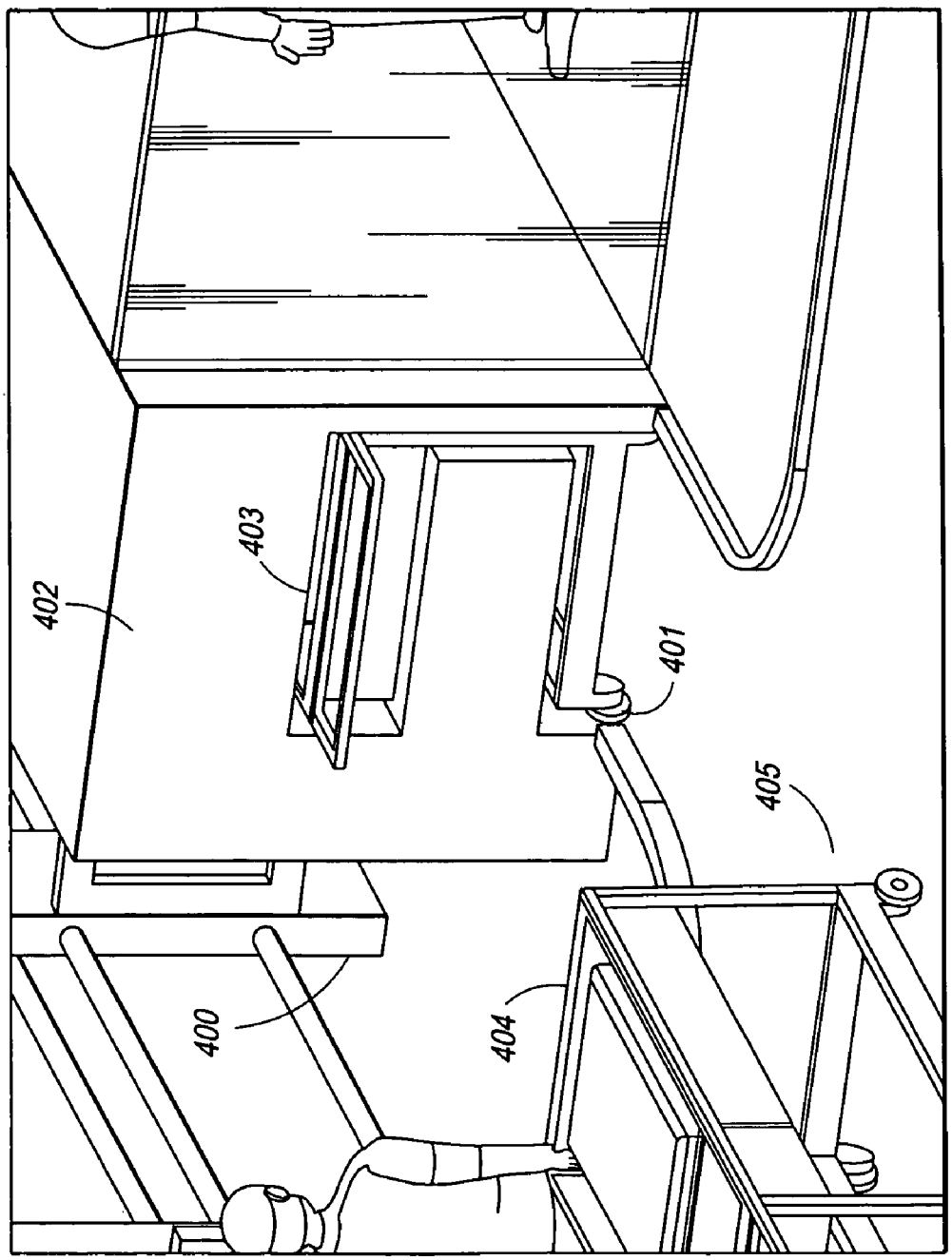
FIG. 4 depicts the X-ray imaging system inspection area entrance in one mode of operation of the integrated carry-on cart and passenger screening station of the present invention.

Referring to FIG. 4, the operational aspects of the inspection area entrance in one embodiment of the integrated carry-on cart and passenger screening station 400 (not shown in its entirety) of the present invention is illustrated. An exemplary carry-on baggage cart or screening cart 404 of the present invention is shown just before it is guided via guide rail conveyance mechanism 401 into the custom-designed entrance 403 of the X-ray imaging system 402. Custom-designed entrance 403 is preferably formed in the same shape as its corresponding screening cart 404. In one embodiment, the entrance to the X-ray imaging system 402 defines a "C"-shaped opening so that the preferred "C"-shaped carry-on baggage cart design, described with respect to FIG. 2 above, is easily guided through the system via guide rail conveyance mechanism 401.

Guide rail conveyance mechanism 401 preferably includes structural rail members placed laterally opposite from one another. Structural rail members preferably comprise protrusions or fingers for physically attaching to the carry-on baggage cart at its distal end 405 to pull the cart through the inspection aperture of X-ray imaging system 402. Thus, the wheels of the carry-on baggage cart are guided through the conveyance mechanism via a guide-rail system with propelling fingers when the scanning process begins. The conveyor speed is controlled to ensure proper resolution of the scanned item when being projected on the operator monitor.

After a passenger loads his or her items onto the carry-on baggage cart, the individual provides loading indications to the system. Such loading indications may be varied, depending upon the operational requirements of the system. In one embodiment, the loading indication is provided by the passenger or the operator pressing a button provided within each loading area. Once depressed, the button advances the carry-on baggage cart through the guide rail system.

In another embodiment, the system employs an electronic mat that automatically signals the start and end of loading the carry-on baggage cart to the system using the weight and exerted pressure by cart and/or individual using the system.

In one embodiment, the system requires the user to swipe a magnetic boarding card to signal the start and finish of loading through card reader machines [not shown] installed at each of the loading areas. Using this technique, the system can track the owner of the items that are deposited for scanning.

Upon receiving a loading indication, the guide rail conveyance mechanism 401 snags, via its finger mechanisms, the leading edge of the cart 404, and pulls it toward custom-designed entrance 403 through X-ray imaging system 402 for screening. The guide rails direct the wheels of the cart 404 through the interior sidewalls of the X-ray imaging system 402. The length and speed of the guide rail conveyance mechanism 401 is chosen so as to give optimum time to the operators to make a decision.

As described with respect to FIG. 3 above, the X-rays are filtered and collimated as they are emitted from the radiation source (not shown in FIG. 4). Subsequently, these rays pass through the contents of the carry-on baggage cart and are then detected by the X-ray detectors (not shown in FIG. 4). The X-rays are then captured by an image intensifier and displayed on a monitor. Further, the captured image is stored in a memory for later processing in order to develop a final image. In one embodiment, the images may be viewed by security personnel. In another embodiment, the images may be "pre-screened" by a computer using mathematically based image processing algorithms. In the event the computer does not detect a threat, the cart is "cleared" immediately. If a potential threat is detected, then the image is sent to a workstation where security personnel can view the image and make a determination of whether the articles in the cart need to be hand searched.

Once scanned, the guide rail conveyance mechanism 401 delivers the scanned carry-on baggage cart 404 to a designated collection point. The collection point may be designated by an operator or controlled automatically and is preferably away from the screening area to avoid congestion. In addition, the collection point may comprise a designated search area for those passengers requiring additional searching, where security personnel perform a manual search of the passenger and their carry-on items. To aid the security personnel in manual searching of items, the X-ray or optical images of the items are displayed on a plurality of search screens, in front of the security personnel. In one embodiment, an operator console is present within the designated search thereby assisting the security personnel to optionally change the display format or orientation of the images displayed on the search screens.

In one embodiment, the operator is given a predetermined time period to inspect the items, after which the system routes the items to a predetermined default, which can be either towards designated area for off-loading carts or towards designated search area, depending on the system settings.

In one embodiment, operators, controlling the system via an operator workstation, can inform users from which designated collection area the individual can retrieve his or her cart containing belongings. One of ordinary skill in the art can appreciate that the selection of site regarding installation of the operator workstations can be made depending upon the specific operational requirements. For instance, and by no way of limitation, operator workstations may preferably be installed either near the X-ray imaging system 402 or remotely located and controlled in a different room entirely. The location and placement of operator workstations does not impose any restriction on the invention itself.

In another embodiment, the system is controlled by a software system that determines the collection point to which the items will be delivered after scanning.

In one embodiment, all the entry points (or X-ray lanes) are assigned a unique number, and each entry point will have a corresponding collection point. Items transferred to the guide rail conveyance mechanism 401 through a particular entry point will be made available only on the collection point corresponding to that entry point. The numbers of each entry point and collection point will be displayed to the users.

In yet another embodiment, the system requires the user to swipe the boarding card, through card reader machines installed at the collection points, before collecting the scanned items. Thus, the system further ensures authenticity of the users before yielding the scanned items. In addition, the system thus prevents the loss of articles due to theft or mistake.

In one embodiment, instead of collecting the scanned items from the collection point corresponding to the entry point used for depositing the items, the user can collect his items from any collection point by swiping his boarding card through the machine installed at that collection point. The term "scanned item", as used here refers to the carry-on baggage cart with passenger belongings on it, but it not limited to such interpretation.

Figure 5:
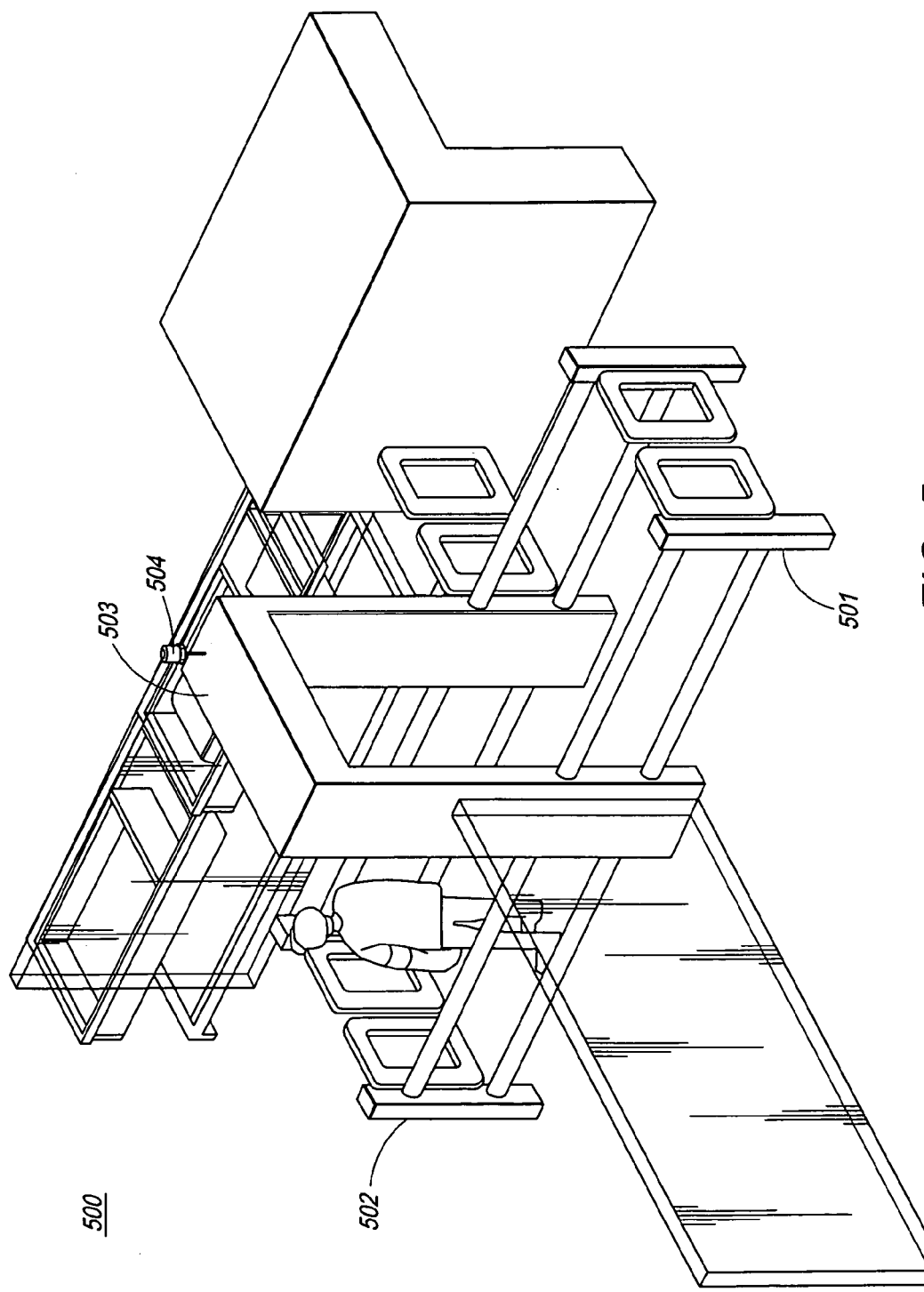
FIG. 5 is a top perspective view of an automated passenger X-ray metal detector in one embodiment of the integrated carry-on cart and passenger screening station of the present invention.

As described with respect to FIG. 5 below, metal detectors and/or trace detectors are employed in the integrated system of the present invention and are used to scan individuals and passengers after they have deposited their belongings for X-ray scanning via the carry-on baggage cart screening system. FIG. 5 is a perspective view of an automated passenger X-ray metal detector in an exemplary embodiment of the present invention. Metal detector 500 is automated to include a controlled entry gate 501 and a controlled exit gate 502. The exit gate is controlled to open upon approach by a passenger as long as the passenger does not trigger an alarm. Upon detection of a threat or item of concern on the body of a passenger as he walks through and under the defined opening 503 of metal detector, the passenger is tagged as suspect and simultaneously an alarm, status signal, or other threat indicator information is communicated to an indicator system 504. Thereafter, the passenger is directed towards a designated search area by a dedicated operator, where the passenger is manually searched by security personnel.

Metal detector 500 may preferably comprise an associated processor 505 (not shown) and a memory 506 (not shown). Optionally, metal detector 500 has an embedded counter incorporated into processor 505 that records and stores the number of people that pass through the metal detector 500 in a given period of time.

In another embodiment, a trace portal may screen passengers. Detection of certain trace materials, including, for example, explosives, contraband traces, or traces of materials that are not contraband but may be associated with contraband or other prohibited activities, such as gun oil, may be used to enhance the security level of the other systems.

In another embodiment, the screening system of the present invention comprises a plurality of screening devices, including, but not limited to, metal detectors, carry-on baggage cart systems as described below, X-ray imaging systems, baggage trace detectors, trace portals, personnel scanners, quadrupole resonance systems, X-ray diffraction systems, and personnel identification systems. The screening devices are optionally in data communication with at least one other screening device and/or a central server. The present invention may include two or more different devices and is not limited in the number or diversity of devices utilized. Data from a plurality of the devices may optionally be integrated to provide a complete picture of the threat level associated with an individual or a baggage, as opposed to being solely evaluated at each device.

In one embodiment, each screening device has an associated memory and processing power that is used to evaluate the threat level associated with an entity, being scanned or detected, and determine the value of assessment data to be transferred preferably to other devices. For example, a passenger screening metal detector may compare obtained scan information with image data stored in memory to determine the threat level associated with an entity and, accordingly, determine the value of assessment data.

Screening devices while in communication exchange information comprising assessment data including, but not limited to, information that provides a quantitative or qualitative assessment of how insecure a detected or screened entity, such as a passenger or a bag, may be. The assessment data is preferably more than a binary alarm indicator. In one embodiment, the assessment data is a numerical value on a scale of ten that corresponds to a specific threat level. The scales for evaluating the threat level can be developed for each device based on prior experience. It must be noted that the design, calibration, and use of such scales, such as those mentioned in the evaluation of threat level of an entity, are routine undertakings of engineering for those of ordinary skill in the art having the benefit of this disclosure consequently they will not be further detailed herein.

In one embodiment, the comparison of obtained scan information with image data stored in memory followed by evaluation of threat level and subsequent determination of assessment data may preferably comprise of cases including, but not restricted to, first, second, and third case etc. in that order, depending upon distinct circumstances arising therein plus corresponding actions taken for the same. Firstly if, for example, the X-ray screening system associates scan data with images resembling objects including, but not limited to, guns, cartridges, weapons, or other dangerous items etc. It can assign a high threat value to the scanned entity and, accordingly, generate assessment data that, regardless of the other assessment data generated by other devices, would trigger an alarm. Secondly if, for example, the X-ray screening system associates scan data with images that resemble low threat items, such as elongated structures or metallic boxes, it can assign a lower threat value to the scanned entity and, accordingly, generate assessment data that may, in combination with assessment from other devices, trigger an alarm. Lastly if, for example, the X-ray system associates scan data with images that resemble negligible threat items, such as clothing, it can assign a minimal threat value to the scanned entity and, accordingly, generate assessment data that will not trigger an alarm.

In another embodiment of the integrated carry-on baggage cart and passenger screening station, facilitating screening of both carry-on luggage placed on the screening cart and individual passengers, a computed tomography (CT) scanner is employed. Thus, the corresponding carry-on baggage cart is designed to facilitate screening via non-"C" shaped scanners, such as, but not limited to CT scanners. In addition, the corresponding carry-on baggage cart is X-ray transmissive to allow for the CT scanner system to scan completely around the cart. While the second embodiment is described with respect to an integrated carry-on baggage cart and passenger screening station in which a CT scanner is employed, it is to be understood by those of ordinary skill in the art that this invention is not limited to such uses, but that any scanning device or mechanism may be used.

CT scanners are being increasingly deployed for securing locations such as airports, as they more accurately recognize chemical and physical properties of scanned objects compared with conventional X-ray scanning systems. A CT scanner rotates completely about the object under inspection.

Figure 6:
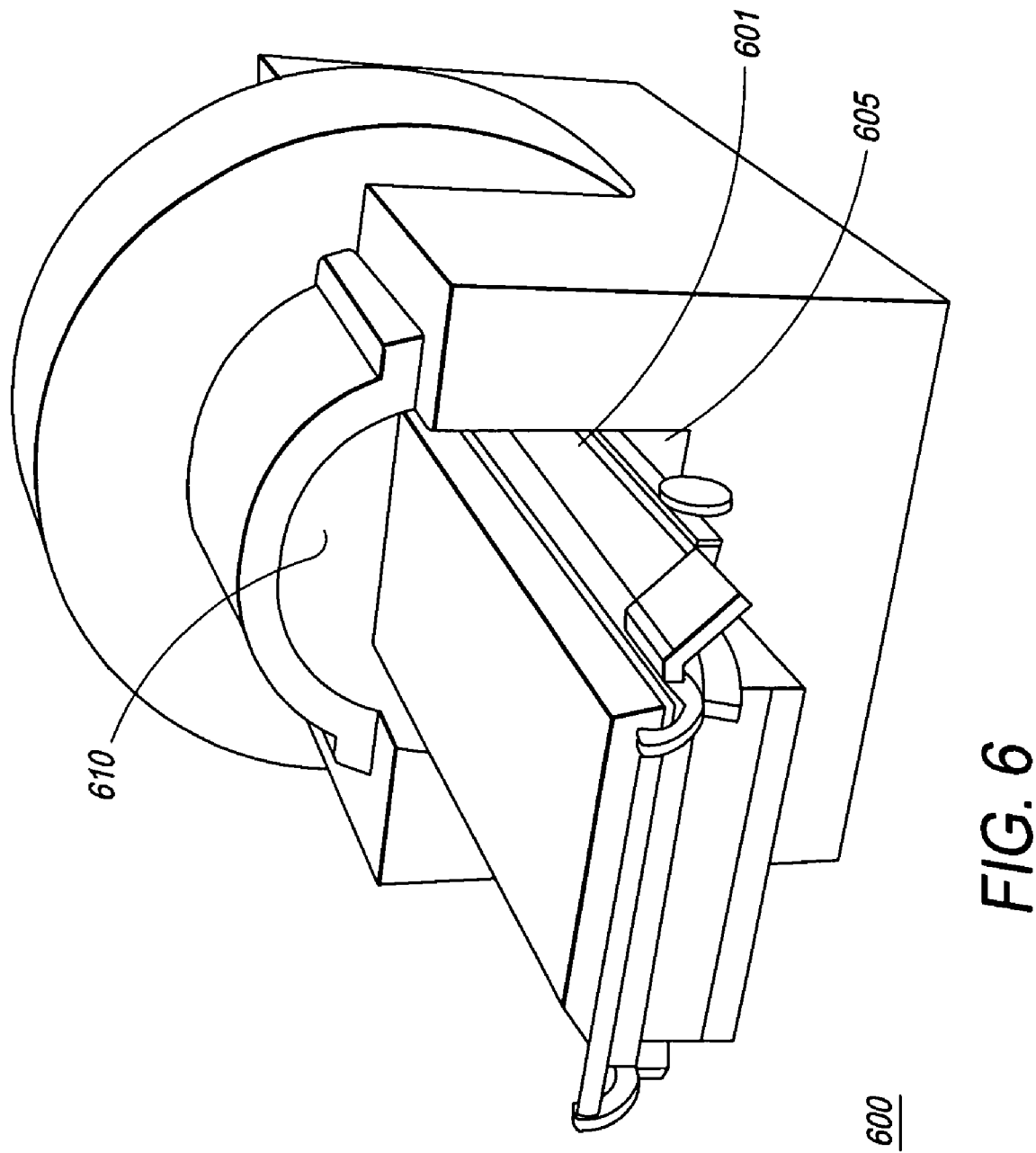
FIG. 6 is a front perspective view of a conventional Computed Tomography (CT) baggage scanning system as used in the integrated carry-on cart and passenger screening station of the present invention.

FIG. 6 is a front perspective view of a conventional Computed Tomography (CT) baggage scanning system as used in the integrated carry-on cart and passenger screening station of the present invention. A typical CT system 600 comprises conveyor gantry 605 and a hollow tube CT scan chamber 610.

The operational characteristics of a CT scanning system are described in further detail with respect to FIG. 8 below and will not be repeated here.

Figure 7:
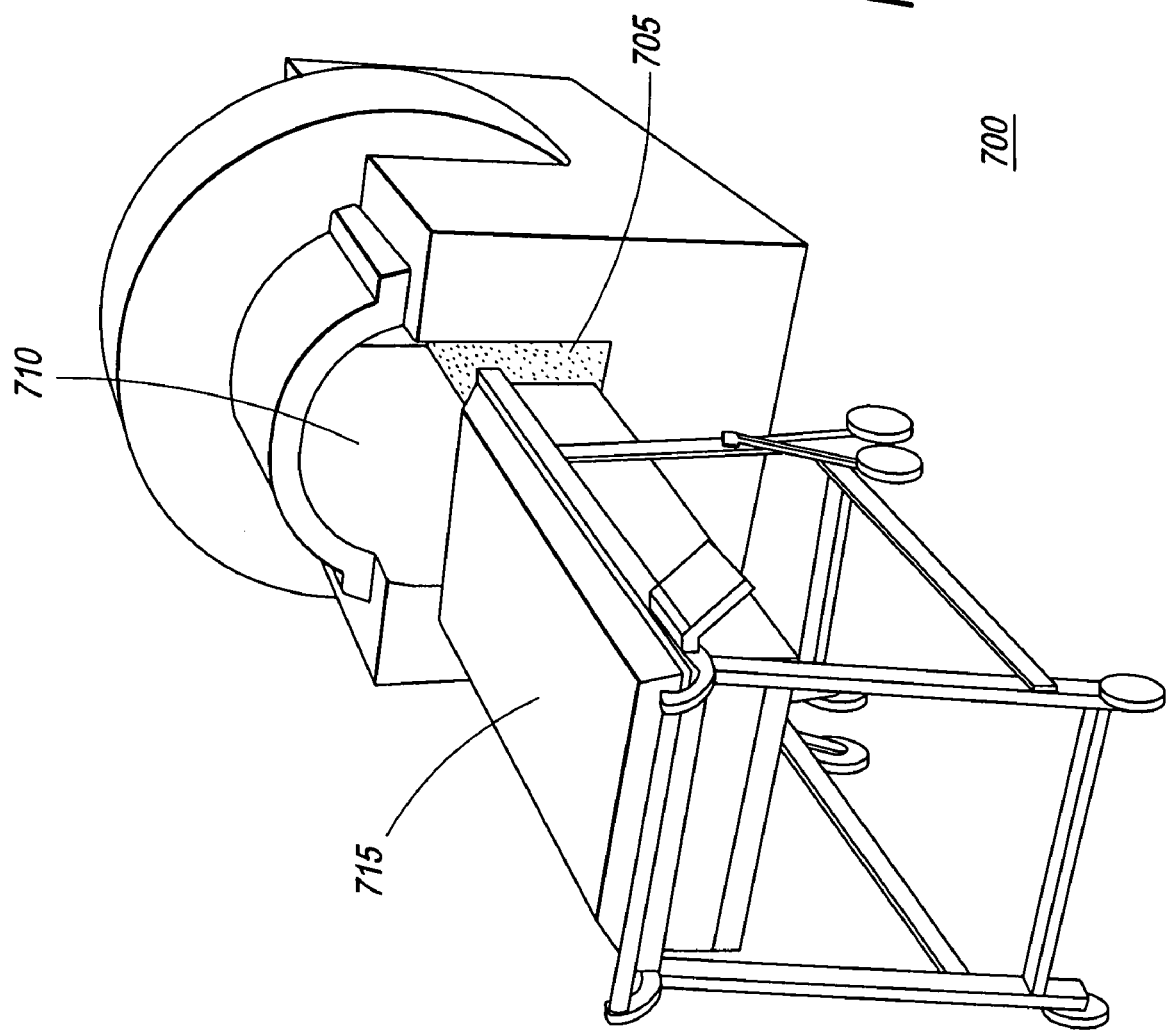
FIG. 7 is a front perspective view of a conventional Computed Tomography (CT) baggage scanning system just prior to receiving a collapsible carry-on cart, as used in the integrated carry-on cart and passenger screening station of the present invention.

FIG. 7 is a front perspective view of a conventional Computed Tomography (CT) baggage scanning system just prior to receiving a collapsible carry-on cart, as used in the integrated carry-on cart and passenger screening station of the present invention. More specifically, FIG. 7 depicts CT scanning system 700 with corresponding carry-on cart 715 positioned for placement onto conveyor gantry 705. As described in further detail below, specially designed carry-on cart 715 is collapsed prior to placement onto conveyor gantry 705. Once collapsed, the pre-positioned and collapsed carry-on cart 715 is placed for entrance into hollow tube CT scan chamber 710.

As shown in FIG. 7, in general operation the carry-on cart preferably loaded with carry-on baggage (not shown) is transported into the hollow tube scan chamber 710 via conveyer 705. Once in the chamber, the baggage is subjected to electromagnetic imaging for generation of two and three-dimensional images. FIG. 8 illustrates a general mode of operation of a conventional CT baggage scanning system.

Figure 8:
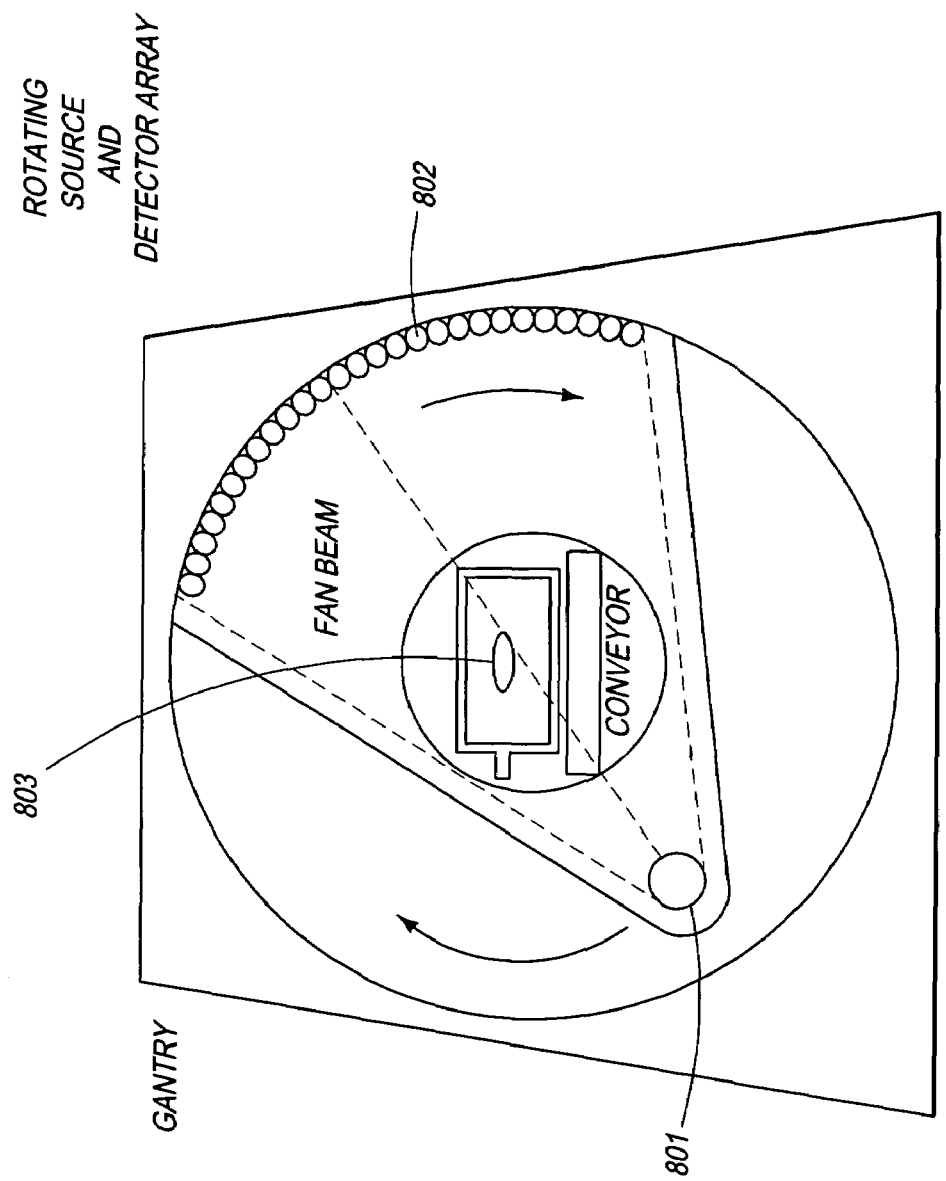
FIG. 8 illustrates a general mode of operation of a conventional CT baggage scanning system.

Referring now to FIG. 8, a conventional CT scanner typically includes a radiation source 801 and a detector array 802. Both radiation source 801 and detector array 802 rotate circumferentially or 360° around object 803 while in scanning operation. Thus, images are obtained from all angles as streams of light are transmitted throughout object 803. The scanner then uses these images to create detailed cross-sectional slices, or tomographs, of specific areas.

Inside the CT chamber, an object is virtually "divided" into three-dimensional units called "voxels." The "voxels" are then used to determine specific object densities and volumes. Based upon density and volume values, the software uses a database with already known values to automatically correlate the mass characteristics of luggage contents to those of potential explosives. If the system finds a match, it alerts the operator, by highlighting suspect areas within the CT slice.

Since CT scanners are slower than conventional baggage-scanning systems, they are not usually employed to scan every piece of luggage; often CT scanning is performed only on items flagged as suspicious during prior inspections. However, precise detection of several dangerous materials, especially explosives, is most effectively carried out with CT scanners. In order to improve the efficiency and throughput of the CT scanning process, the screening system of present invention allows for all baggage placed on a carry-on cart associated with a passenger to be screened simultaneously.

Figure 9A:
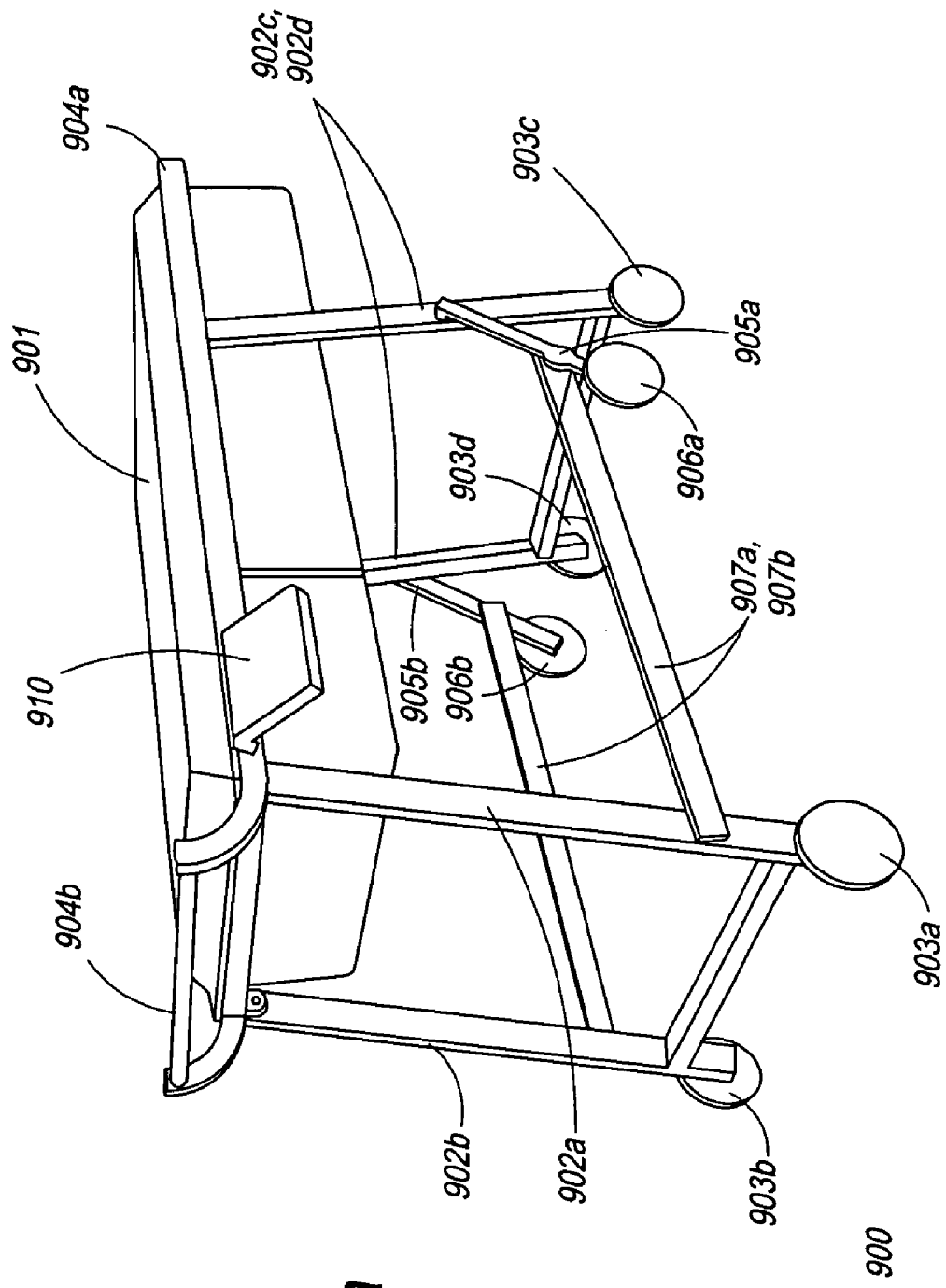
FIG. 9a is a perspective view of one embodiment of a carry-on baggage cart as employed in the present invention, in an extended configuration.

Referring back to FIG. 6, in operation, the carry-on baggage cart 601 is loaded onto conveyor gantry 605, which transports the cart into the CT scanning chamber. Thus, the carry-on cart is a sturdy, transportable luggage cart. Preferably, the legs on the cart are collapsible to allow for ease of entrance into the CT scanning chamber. FIG. 9a is a perspective view of one embodiment of a carry-on baggage cart as employed in the present invention, in an extended configuration.

Referring now to FIG. 9a, carry-on baggage cart 900 comprises a top part 901, such as, but not limited to a board, compartment, or drawer for holding the baggage and/or carry-on items. Carry-on baggage cart further comprises cart legs 902a, 902b, 902c, and 902d. The distal ends of legs 902a-902d are fitted with wheels 903a, 903b, 903c, 903d. The proximate ends of legs 902a-902d are movably attached to top frame 904a. In addition, top frame 904a comprises handle 904b for easy maneuvering of the carry-on baggage cart 900. Top part 901 is preferably designed such that it can be connected to top frame 904a and handle 904b. In addition, carry-on baggage cart 900 preferably comprises supplementary cart legs 905a and 905b, which in one embodiment are movably attached to cart legs 902c and 902d at their proximate ends. Supplementary wheels 906a and 906b are fixedly attached to the distal ends of supplementary cart legs 905a and 905b and are preferably provided for maneuvering the cart in a collapsed configuration, as described in greater detail below with respect to FIG. 9b. Supplementary cart legs 905a and 905b equipped with supplementary wheels 906a and 906b are fixedly attached to cart legs 902a and 902b via horizontal cart leg support braces 907a and 907b. In one embodiment, horizontal cart leg support braces 907a and 907b provide a structural support for the collapsed carry-on baggage cart. In one embodiment, carry-on baggage cart further comprises display screen 910, which is described in greater detail below with respect to the security enhancement feature of this innovation.

Figure 9B:
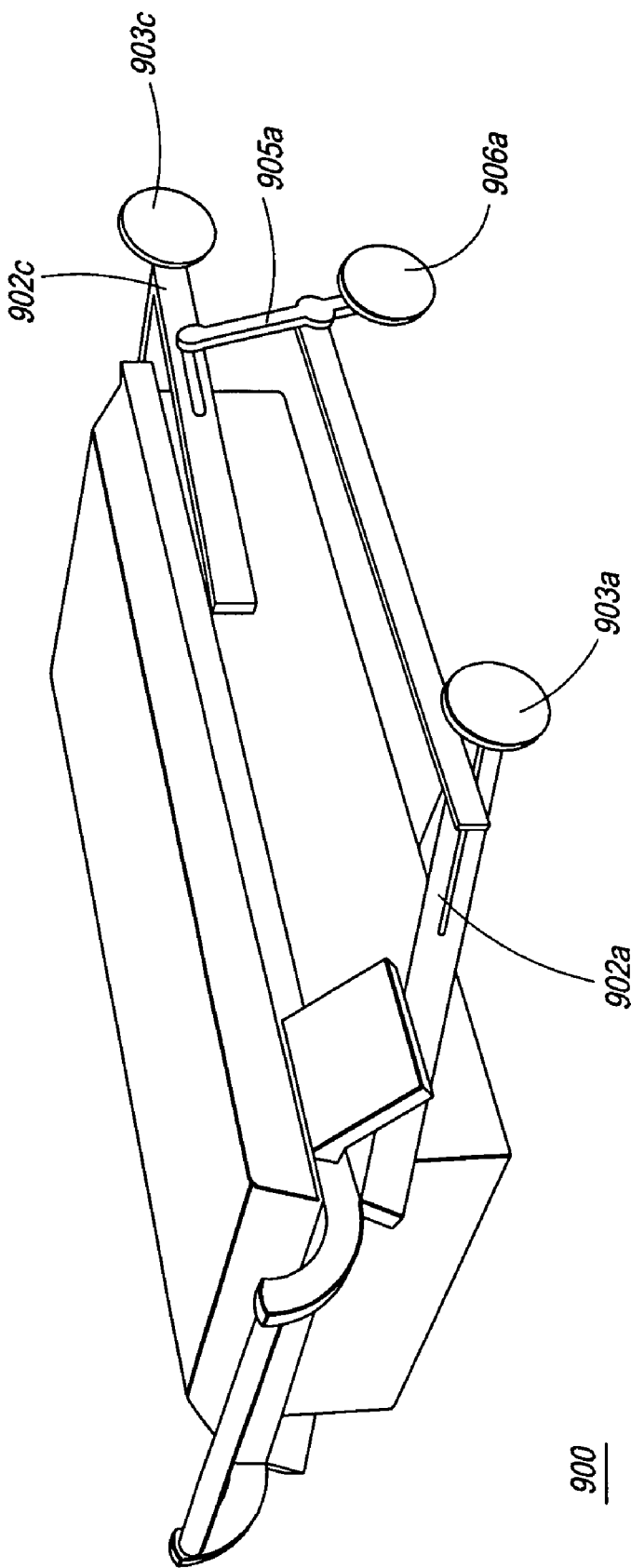
FIG. 9b is a perspective view of one embodiment of a carry-on baggage cart as employed in the present invention, in a collapsed or retracted configuration.

Referring now to FIG. 9b, a perspective view of one embodiment of a carry-on baggage cart as employed in the present invention is depicted. FIG. 9b illustrates a side view of the carry-on baggage cart 900 in a collapsed configuration. In one embodiment, to allow for easy loading of the cart onto the conveyor of a CT scanner, cart legs 902a-d are movably attached to top frame 904a and handle 904b to allow for the carry-on cart to easily collapse. Thus, the cart legs 902a-902d along with wheels 903a-903d may be retracted, or collapsed, on the underside of the cart (not shown) prior to loading onto the conveyor, for facile transportation through the conveyor. In addition, when cart legs 902a, 902b, 902c, and 902d are collapsed, supplementary cart legs 905a and 905b extend and become operable along with supplementary wheels 906a and 906b. Cart legs 902a and 902b assume an angled position, yet remain in operation when cart 900 is in a collapsed configuration. Cart legs 902c (shown in FIG. 9b) and 902d (not shown) are in a stowed position and are not in operation when then cart is collapsed.

Additionally, carry-on baggage cart 900 is provided with a lock and release mechanism (not shown) for locking the cart legs 902a-902d and wheels 903a-903d in either a retracted or extended position. The lock and release mechanism is preferably controlled by a handle or a push button (not shown) provided on the cart, which may be operated by the passenger whose luggage is to be scanned or by an operator, after the individual indicates that loading of baggage on the cart has finished.

Figure 10:
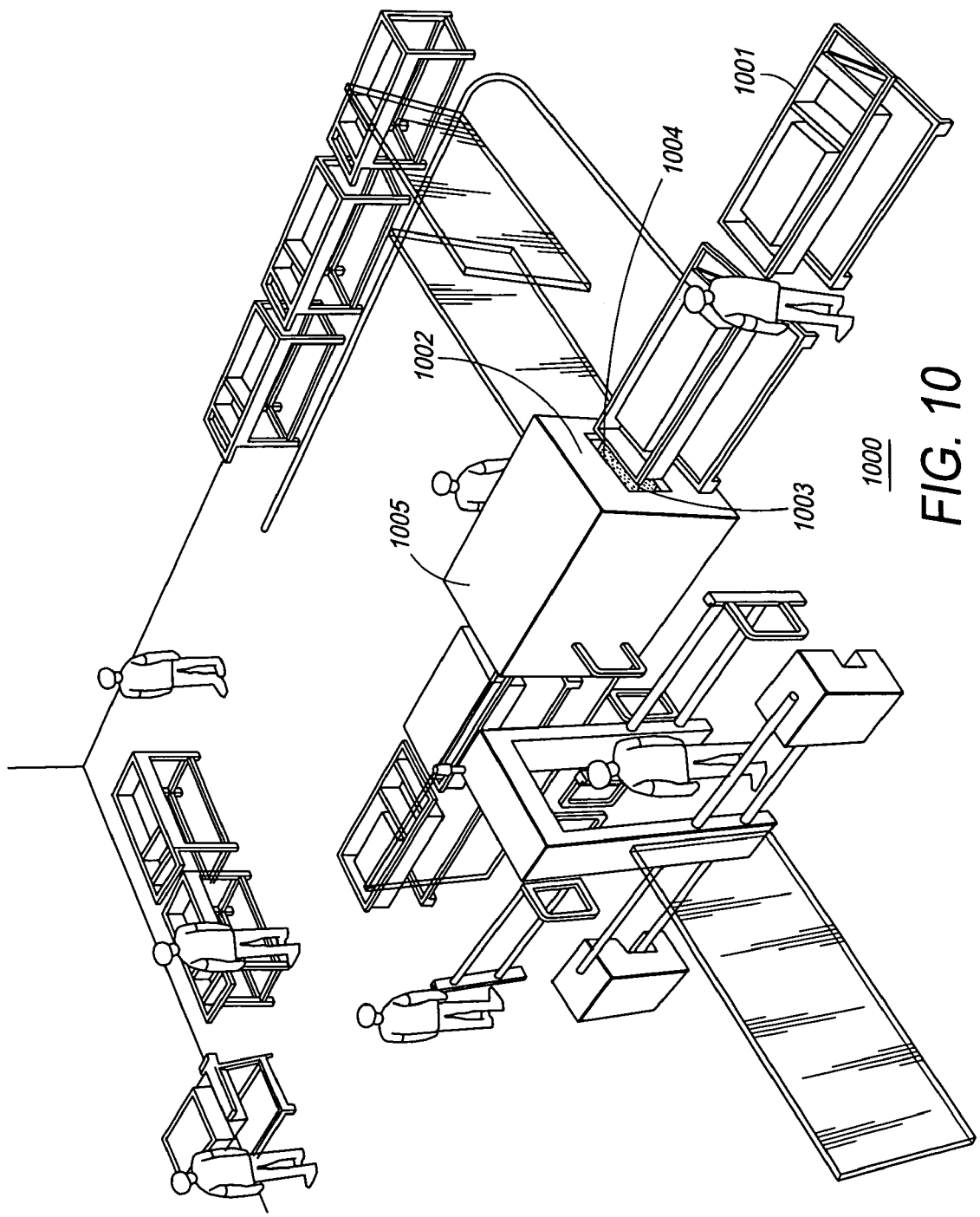
FIG. 10 is a top perspective view of one exemplary embodiment and functional layout of an integrated carry-on baggage cart and passenger screening station, facilitating screening of both carry-on luggage placed on the screening cart and individual passengers.

FIG. 10 is a top perspective view of one exemplary embodiment and functional layout of an integrated carry-on baggage cart and passenger screening station 1000, facilitating screening of both carry-on luggage placed on the screening cart and individual passengers. Thus, in operation, an individual passenger loads the carry-on baggage cart 1001 containing his or her luggage and moves it toward the entrance 1002 of a CT scanning system 1005 for screening. Here, the individual or operator uses the control on the cart (not shown), thus causing the cart legs to retract or collapse. The cart can then be transported onto the conveyor 1003 provided at the entrance 1002 of the CT scanning system. Preferably, the loading end of the conveyor belt is located proximate to the floor level. The conveyor is then graded upwards to transport the cart into the CT scanning chamber 1004, as shown in FIG. 10. The conveyor mechanism allows for convenient loading of the cart, with minimal physical effort on the part of the individual or the operator.

In an alternate embodiment, the entrance of the CT scanning system may be designed such that the inlet to the scanning chamber is at floor level. In this embodiment, a guide-rail mechanism may be used to pull the cart into the scanner entrance, as previously described with respect to the first embodiment of the present invention.

Preferably, the carry-on baggage cart is designed to allow for the carts to be stacked or inserted into one another when not in use. This provides for easy and space-saving storage of carts.

As previously mentioned, the process of CT scanning involves a complete circumferential (360°) rotation by the illuminating source and detectors about the object under inspection. In order to allow irradiation and imaging from all angles, the carry-on baggage cart is designed to be completely X-ray transmissive. Preferably, the entire cart, including legs, wheels, and handle is manufactured using a suitable X-ray transmissive material or combination thereof. Such X-ray transmissive materials include, but are not limited to, carbon fiber or transparent synthetic resin, or any other sturdy plastic.

Figure 11:
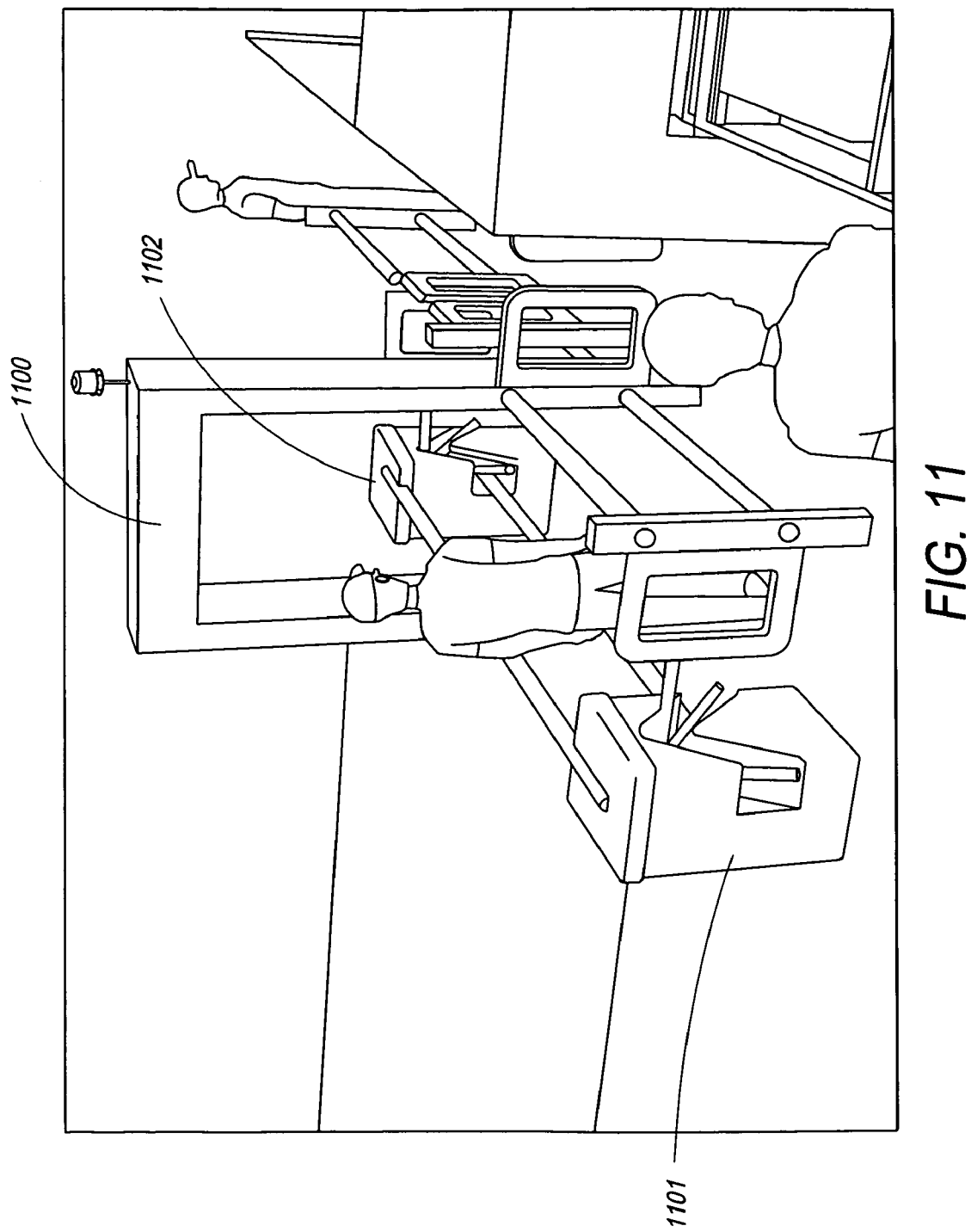
FIG. 11 depicts an exemplary passenger screening station of the present invention, in which a turnstile is employed to facilitate passenger entrance and exit.

As described with respect to FIG. 5 above, metal detectors and/or trace detectors are employed in the integrated system of the present invention and are used to scan individuals and passengers after they have deposited their belongings for X-ray scanning via the carry-on baggage cart screening system. FIG. 11 depicts an exemplary passenger screening station of the present invention, in which an automated passenger X-ray metal detector further comprising a turnstile is employed.

Now referring to FIG. 11, in one embodiment, metal detector 1100 is automated to include a controlled entry turnstile 1101 and a controlled exit turnstile 1102. The exit turnstile 1002 is controlled to open upon approach by a passenger as long as the passenger does not trigger an alarm. Upon detection of a threat or item of concern on the body of a passenger as he walks through and under the defined opening of the metal detector, the passenger is tagged as suspect and simultaneously an alarm, status signal, or other threat indicator information is communicated to an indicator system (not shown). Thereafter, the passenger is directed towards a designated search area by a dedicated operator, where the passenger is manually searched by security personnel.

Metal detector 1100 preferably comprises an associated processor (not shown) and a memory (not shown). Optionally, metal detector 1100 has an embedded counter incorporated into the processor that records and stores the number of people that pass through the metal detector 1100 in a given period of time.

In another embodiment, a trace portal may screen passengers. Detection of certain trace materials, including, for example, explosives, contraband traces, or traces of materials that are not contraband but may be associated with contraband or other prohibited activities, such as gun oil, may be used to enhance the security level of the other systems.

In one embodiment, the integrated carry-on cart and passenger screening station of the present invention further comprises enhanced security. In one embodiment, the security enhancement comprises a method for identifying a passenger and associating the identified passenger with a corresponding carry-on baggage cart. In an exemplary embodiment, the security enhancement features of the present invention include identifying a passenger via a bar code, such as, but not limited to, a bar code on a boarding pass. The identified passenger is then associated with a carry-on baggage cart wherein the passenger identification is read by a bar code reader located at a cart access station. The passenger, already equipped with a current boarding pass from an authorized agent (such as airline personnel), passes the boarding pass underneath the bar code reader. The bar code reader then registers the information from the bar code on the boarding pass into a database, associates a cart with a passenger. Once associated with a passenger, the cart is subsequently released to the passenger.

It should be noted however, that a passenger can be identified via many identification methods, such as using personal forms of identification, which include, but are not limited to, a credit card, driver's license, state identification card, passport, or any accepted form of identification as are well-known to those of ordinary skill in the art. The personal identification means may be read by a corresponding identification reading means, including, but not limited to, a magnetic card reading device, a credit card reader, or any accepted means for accepting identification as are well-known to those of ordinary skill in the art.

The passenger identification can also be read by security personnel. In this embodiment, security personnel manually inspect the personal identification and if the identification is accepted, push a button to release the associated carry-on baggage cart to the passenger.

In one embodiment, both a boarding pass with a bar code and a personal identification means may be used to associate a passenger with a carry-on cart. In this embodiment, security personnel can compare the identification displayed on the carry-on baggage cart with the personal identification and subsequently release the cart to the passenger.

Referring back to FIG. 9, in one embodiment, carry-on baggage cart further comprises small computer and display screen 910, for displaying the association information scanned from the passenger boarding pass onto the carry-on baggage cart. The information includes, but is not limited to, passenger name and flight information. This physically identifies a particular passenger with a particular cart, and thus the passenger is associated with his or her belongings. As noted above, if a passenger is identified via any other identification method, such as using personal forms of identification, such identification information may also be displayed on the small computer and display screen 910.

Figure 12:
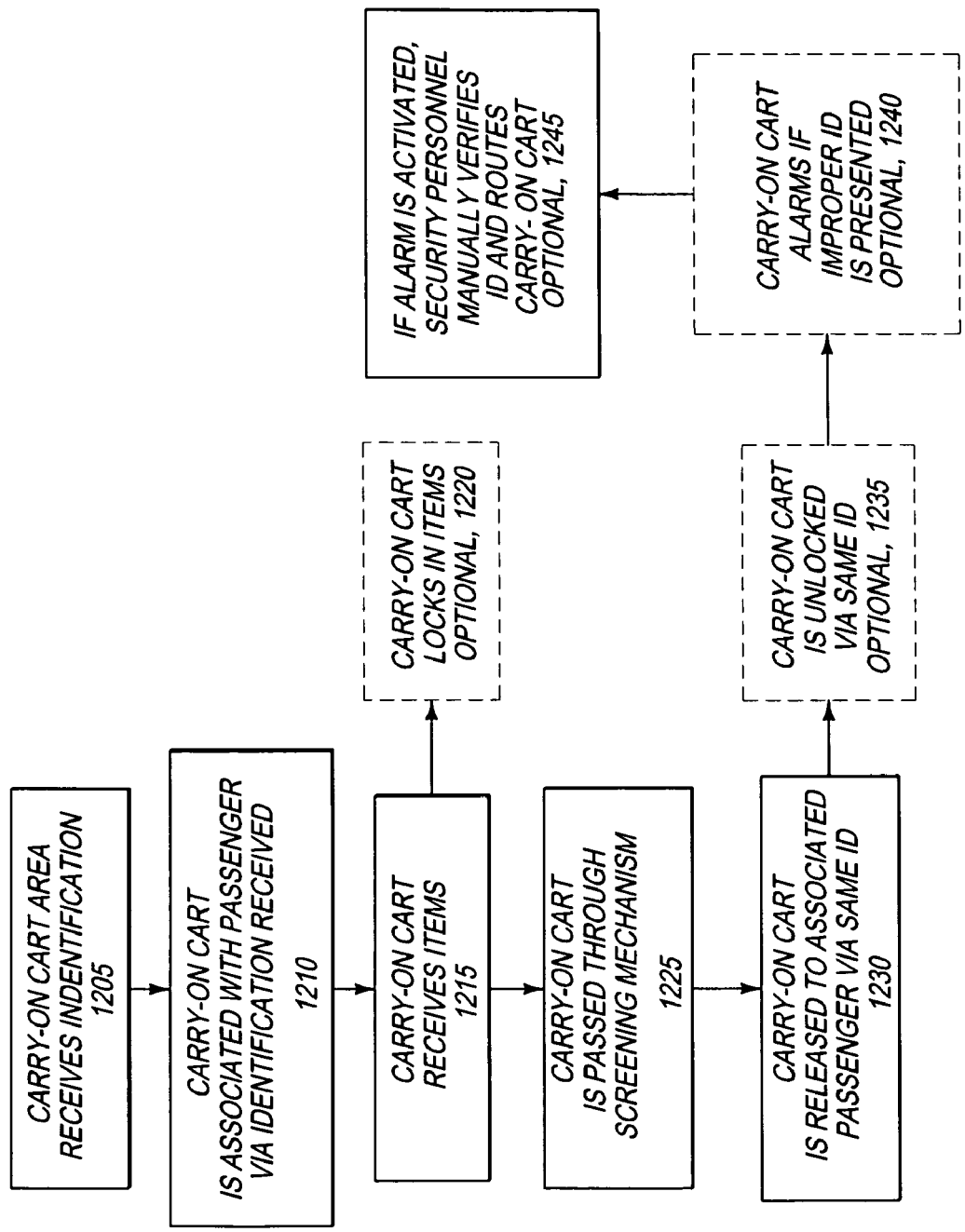
FIG. 12 is a flowchart depicting exemplary operational steps in the security enhancement mechanism of the integrated carry-on baggage cart and passenger screening station of the present invention.

FIG. 12 is a flowchart depicting exemplary operational steps in the security enhancement mechanism of the integrated carry-on baggage cart and passenger screening station of the present invention. As shown in FIG. 12, in step 1205, the carry-on cart access area receives identification from a person to be screened. Such identification methods are described in detail above and will not be repeated herein. Once identification means are received, a carry-on baggage cart is associated with a passenger via the identification received, as shown in step 1210. In step 1215, the passenger or person to be screened places his or her items on the carry-on baggage cart.

In one embodiment, the carry-on cart employed in the present invention may further comprise a cover. In one embodiment, the cover further comprises a roll-top or netting. In an optional step 1220, the cover automatically locks when the passenger closes it after he finishes the divestiture process. Thus, the items are kept safe from theft, especially where items of value, such as jewelry and laptops are concerned.

In step 1225, the carry-on cart is passed through the screening mechanism. The various embodiments of the carry-on cart screening mechanism have been described in detail with respect to the embodiments above and will not be described in detail herein.

In step 1230, after the scanning process is complete, the carry-on cart may be released to the associated passenger if the identification received by the cart matches that associated with the cart. If the carry-on baggage cart is positively identified with a particular passenger, then in an optional step 1235, the carry-on cart is unlocked. The passenger can "unlock" the cart cover by simply waving the bar code on his boarding pass underneath the bar code reader that is fixedly attached to the small computer on the cart.

If the wrong identification is presented to the carry-on baggage cart, and the cart cannot be positively associated with the passenger presenting the identification, in optional step 1240, an alarm may sound. If an alarm is activated, security personnel agents will intervene, as shown in step 1245. Security personnel agents can also manually deactivate the alarm. The security personnel agent will manually verify the identification or re-route the cart to the correct passenger.

If the cart is flagged by the scanning system as containing a potential threat, the boarding pass or other identification and association means is rendered ineffective and security personnel agents are in control of the cart. In one embodiment, security personnel agents may manually unlock the cart cover for manual inspection of its contents.

In one embodiment, the cart may transmit identification information to security personnel wirelessly. Thus, the identification information is transmitted to the security personnel agent at the carry-on baggage cart screening station and also the security personnel screener at the passenger screening station. Thus, the security personnel agents can confirm, in real-time, that the carry-on cart and a passenger walking through the passenger screening device are associated. The security personnel agents can then compare the passenger identification to the information received at their respective screening stations.

The above examples are merely illustrative of the many applications of the system of present invention. Although only a few embodiments of the present invention have been described herein, it should be understood that the present invention might be embodied in many other forms without departing from the spirit or scope of the invention. Therefore, the present examples and embodiments should be considered as illustrative and not restrictive, and the invention may be modified within the scope of the appended claims.

I claim:

1. A system for conducting security comprising;
an X-ray scanning system having an entrance;
a screening cart having a frame assembly, computer, and display for receiving and displaying passenger information;
a conveyor to direct a screening cart passing through the X-ray scanning system; and
a reader to associate a person to be screened with said screening cart.

2. The system of claim 1 wherein the frame assembly has collapsible legs.

3. The system of claim 2 wherein the legs of the frame assembly are collapsed prior to being transported by said conveyor.

4. The system of claim 2 wherein the legs of the frame assembly are expanded after being transported by said conveyor.

5. The system of claim 1 wherein the frame assembly physically complements the entrance and an internal configuration of said X-ray scanning system.

6. The system of claim 1 further comprising a module to integrate data collected from both the X-ray scanning system and passenger screening device to generate overall threat assessment.

7. The system of claim 1 wherein said X-ray scanning system comprises a radiation source and a detector array.

8. The system of claim 7 wherein said radiation source is a dual energy source.

9. The system of claim 1 wherein the screening cart is comprised of an X-ray transmissive material.

10. The system of claim 1 further comprising an integrated screening station comprising a central server, a processor and a memory in data communication with the X-ray scanning system and the passenger screening device.

11. A system for conducting security comprising;
a CT scanning system having an entrance;
a screening cart having a frame assembly, computer, and display for receiving and displaying passenger information;
a conveyor to direct a screening cart passing through the CT scanning system; and
a reader to associate a person to be screened with said screening cart.

12. The system of claim 11 wherein the frame assembly has collapsible legs.

13. The system of claim 12 wherein the legs of the frame assembly are collapsed prior to being transported by said conveyor.

14. The system of claim 12 wherein the legs of the frame assembly are expanded after being transported by said conveyor.

15. The system of claim 11 wherein the frame assembly physically complements the entrance and an internal configuration of said CT scanning system.

16. The system of claim 11 wherein the screening cart is comprised of an X-ray transmissive material.

17. The system of claim 11 further comprising an integrated screening station comprising a central server, a processor and a memory in data communication with the CT scanning system and the passenger screening device.

* * * * *